United States Patent [19]
Stinton

[11] Patent Number: 5,204,670
[45] Date of Patent: Apr. 20, 1993

[54] ADAPTABLE ELECTRIC MONITORING AND IDENTIFICATION SYSTEM

[75] Inventor: Vincent D. Stinton, Brighton, Colo.

[73] Assignee: B. I. Incorporated, Boulder, Colo.

[21] Appl. No.: 572,905

[22] Filed: Aug. 23, 1990

Related U.S. Application Data

[63] Continuation-in-part of Ser. No. 237,860, Aug. 29, 1988, Pat. No. 4,952,928.

[51] Int. Cl.$^5$ .............................................. H04B 5/00
[52] U.S. Cl. ............................... 340/825.54; 340/573; 340/825.49
[58] Field of Search ........... 340/539, 573, 576, 825.49, 340/825.54; 180/272; 379/30, 40; 128/644, 668, 721, 901, 902, 903

[56] References Cited

U.S. PATENT DOCUMENTS

| | | | |
|---|---|---|---|
| 3,253,588 | 5/1966 | Vuilleumier et al. | |
| 3,478,344 | 11/1969 | Schwitzgebel et al. | |
| 3,618,067 | 11/1971 | DeVale et al. | |
| 3,639,907 | 2/1972 | Greatbatch | |
| 3,764,270 | 10/1973 | Collier et al. | 23/255 |
| 3,882,277 | 5/1975 | DePedro et al. | |
| 3,882,278 | 5/1975 | Coll | |
| 3,898,984 | 8/1975 | Mandel et al. | 128/2.1 A |
| 3,947,832 | 3/1976 | Rosgen et al. | 390/224 |
| 4,112,421 | 9/1978 | Freeny, Jr. | 343/112 D |
| 4,136,338 | 1/1979 | Antenore | 340/551 |
| 4,259,665 | 3/1981 | Manning | 340/575 |
| 4,260,982 | 4/1981 | DeBenedictis | 340/539 |
| 4,342,986 | 8/1982 | Buskirk et al. | 340/539 |
| 4,347,501 | 8/1982 | Akerberg | 340/539 |
| 4,371,752 | 2/1983 | Matthews et al. | |
| 4,428,378 | 1/1984 | Anderson et al. | 128/419 |
| 4,475,481 | 10/1984 | Carroll | 119/51 R |
| 4,494,119 | 1/1985 | Wimbush | 343/457 |
| 4,494,553 | 1/1985 | Sciarra | 128/721 |
| 4,559,526 | 12/1985 | Tani et al. | 340/539 |
| 4,593,273 | 6/1986 | Narcisse | 340/539 |
| 4,598,275 | 7/1986 | Ross et al. | 340/573 |

(List continued on next page.)

FOREIGN PATENT DOCUMENTS

| | | | |
|---|---|---|---|
| 965179 | 3/1975 | Canada | 349/31 |
| 0010611 | 9/1979 | European Pat. Off. | |
| 8210405 | 6/1982 | France | |

OTHER PUBLICATIONS

Schwitzgebel, R. K., "Issues in the use of an Electric Rehabilitation System with Chronic Recidivists", *Law and Society Review*, 3:597-611 (1969).

(List continued on next page.)

Primary Examiner—Donald J. Yusko
Assistant Examiner—Dervis Magistre
Attorney, Agent, or Firm—Fitch, Even, Tabin & Flannery

[57] ABSTRACT

A personnel monitoring system includes a host central processing unit, or CPU, maintained by a supervising agency that automatically, or by request, receives and interprets data from individuals being monitored. The monitored individuals may wear or carry a transmitting or transponding unit that periodically, or upon request, transmits a uniquely encoded signal that identifies the person being monitored, as well as information about the condition or activities of the person being monitored. Lower risk monitored individuals may be required to simply contact the host CPU on a regular basis, e.g., weekly, monthly, or yearly. The host CPU includes a plurality of software submodules that can be selectively installed therein to allow a desired monitoring configuration to be used in order to best meet the needs of the monitoring agency. The communication link between the individual and the CPU may be by way of existing telephone lines or other telecommunicative links. From data received, the host CPU generates desired reports indicating the location, condition, status, and/or activities of the monitored individual.

12 Claims, 10 Drawing Sheets

U.S. PATENT DOCUMENTS

| | | | |
|---|---|---|---|
| 4,622,544 | 11/1986 | Bially et al. | 340/636 |
| 4,631,708 | 12/1986 | Wood et al. | 367/2 |
| 4,656,463 | 4/1987 | Anders et al. | 340/572 |
| 4,658,357 | 4/1987 | Carroll et al. | 364/406 |
| 4,665,387 | 5/1987 | Cooper et al. | 340/572 |
| 4,675,656 | 6/1987 | Narcisse | 340/539 |
| 4,709,704 | 8/1986 | Lukasiewicz | 128/644 |
| 4,747,120 | 5/1988 | Foley | 379/38 |
| 4,814,751 | 3/1989 | Hawkins et al. | 340/573 |
| 4,819,860 | 4/1989 | Hargrove et al. | 228/668 |
| 4,827,943 | 5/1989 | Bornn et al. | 128/668 |
| 4,837,568 | 6/1989 | Snaper | 340/825 |
| 4,843,377 | 6/1989 | Fuller et al. | 340/573 |

OTHER PUBLICATIONS

Ingraham, et al., "Controlling Human Behavior with Electronics", *The Futurist*, pp. 60–62 (1970).

Schwitzgebel, et al., "Methods and Designs" *Behav. Res. Meth. & Instru.*, 2:99–105 (1970).

Meyer, "Crime Deterrent Transponder System", *IEEE Transactions on Aerospace and Electronic Systems*, AES-7:1, 2–22 (Jan. 1971).

Schmidt, et al., "Electronics Monitors", in Intermediate Punishments: Intensive Supervision, Home Confinement and Electronic Surveillance; *Issues in Crime and Justice*, 2:137–152 (Belinda R. McCarthy, Editor) (Criminal Justice Press, Monsey, NY 1987).

Vaughn, "Planning for Change; The Use of Electronic Monitoring as a Correctional Alternative", in Intermediate Punishments: Intensive Supervision, Home Confinement and Electronic Surveillance; *Issues in Crime and Justice*, 2:153–168 (Belinda R. McCarthy, Editor) (Criminal Justice Press, Monsey NY 1987).

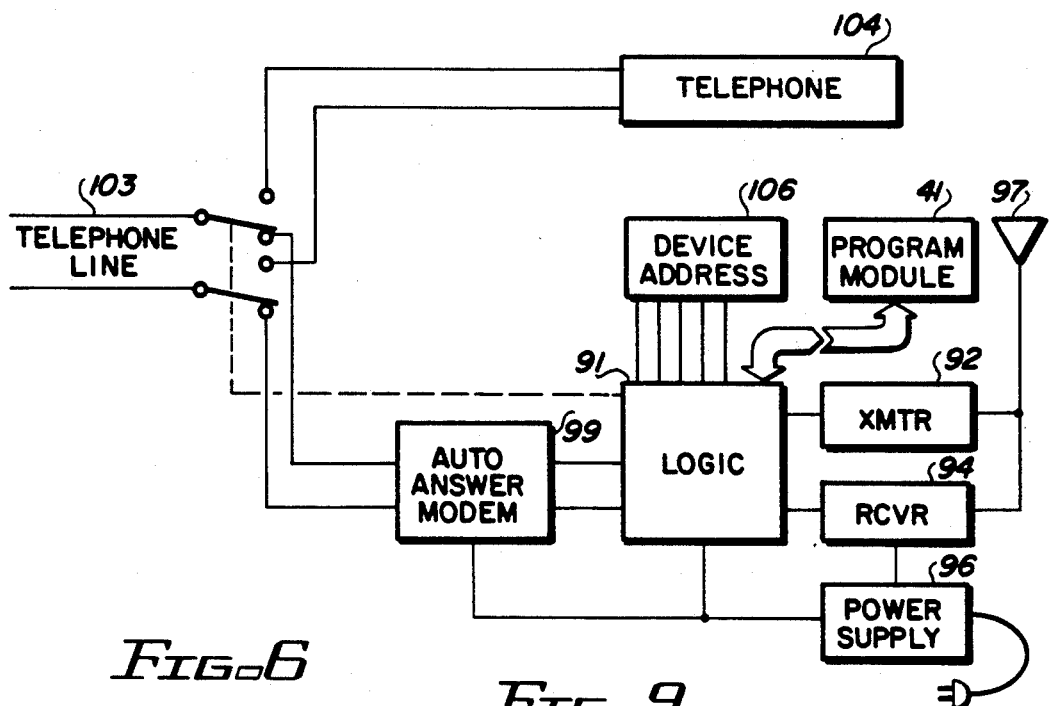
FIG. 6
FIG. 9
| | SLEEP | EAT | WORK | ALCOHOL | COCAINE | VIOLENCE |
|---|---|---|---|---|---|---|
| TEMPERATURE | − | − | +++ | + | − | − |
| HEART RATE | − | + | +++ | + | + | + |
| LEG SIZE | O | − | + | ++ | − | − |
| ACTIVITY | O | O | +++ | +− | +− | +++ |
| VERBAL | O | O | + | + | + | ++ |
| POSTURE | − | | | | | \ | \ | | |
| BLOOD PRESSURE | − | + | +++ | +++ | +++ | +++ |
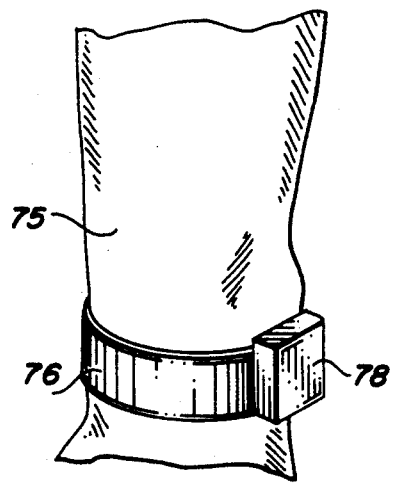
FIG. 10A
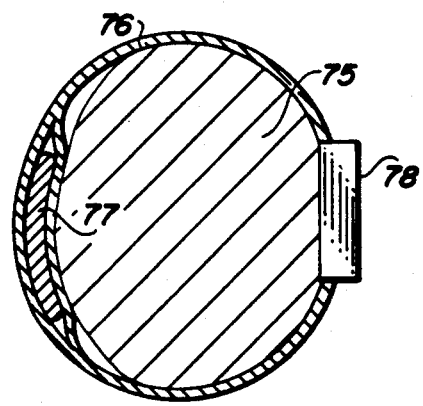
FIG. 10B

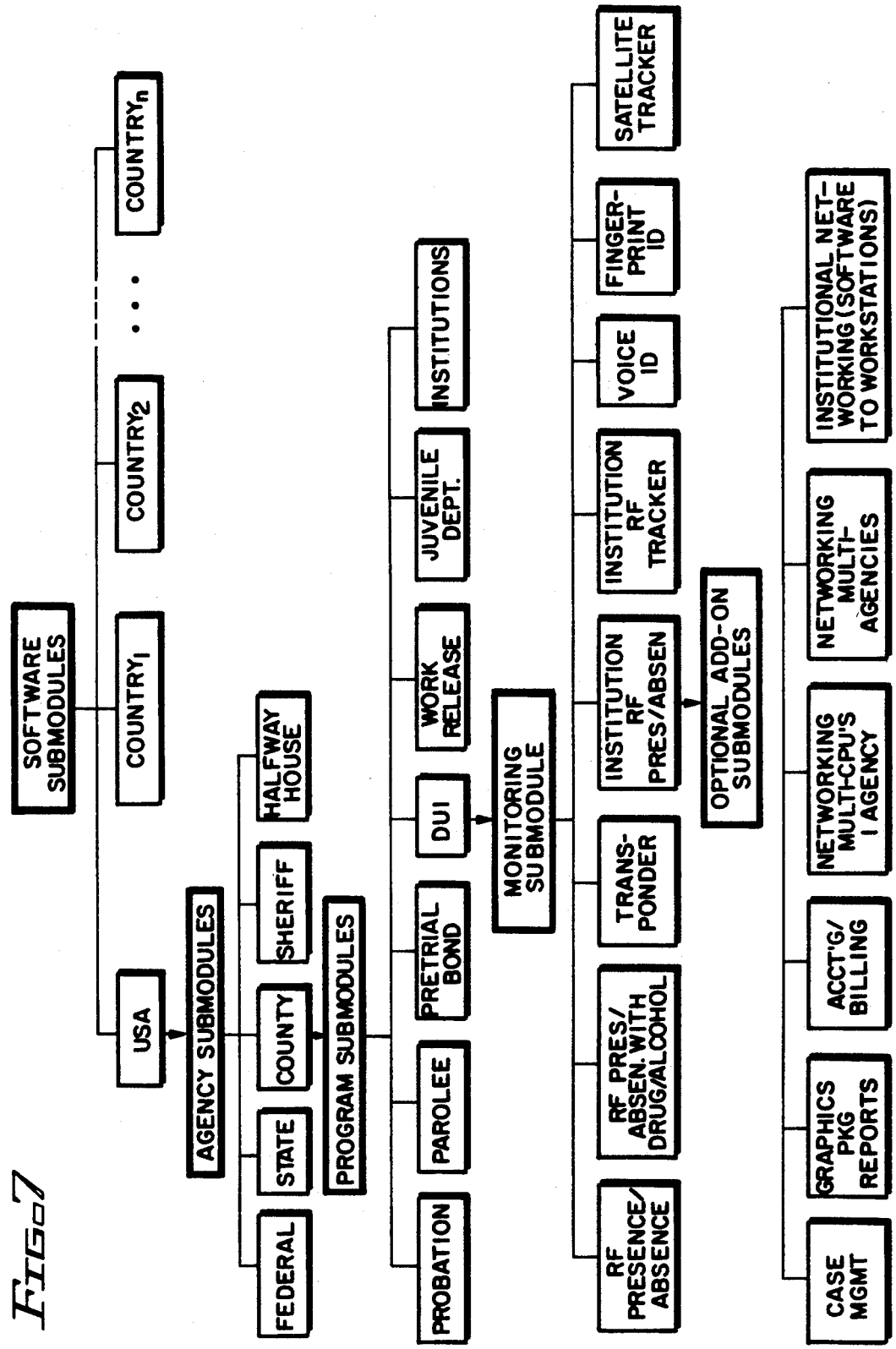

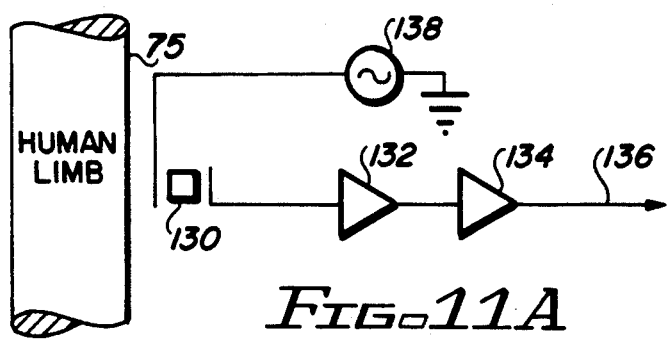
FIG. 11A
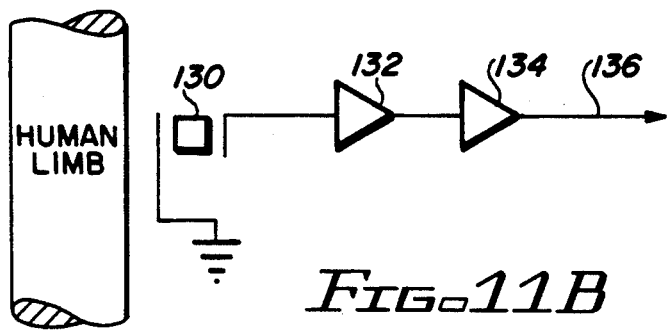
FIG. 11B
FIG. 12
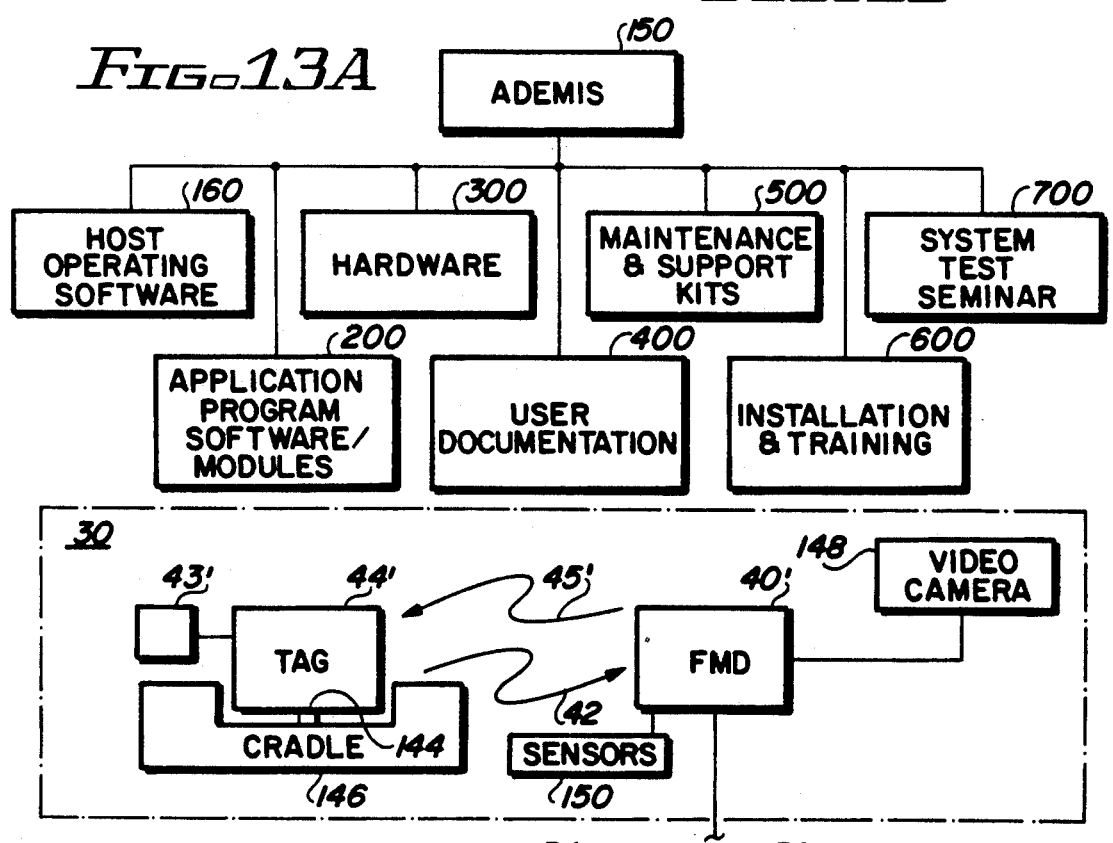
FIG. 13A
FIG. 14

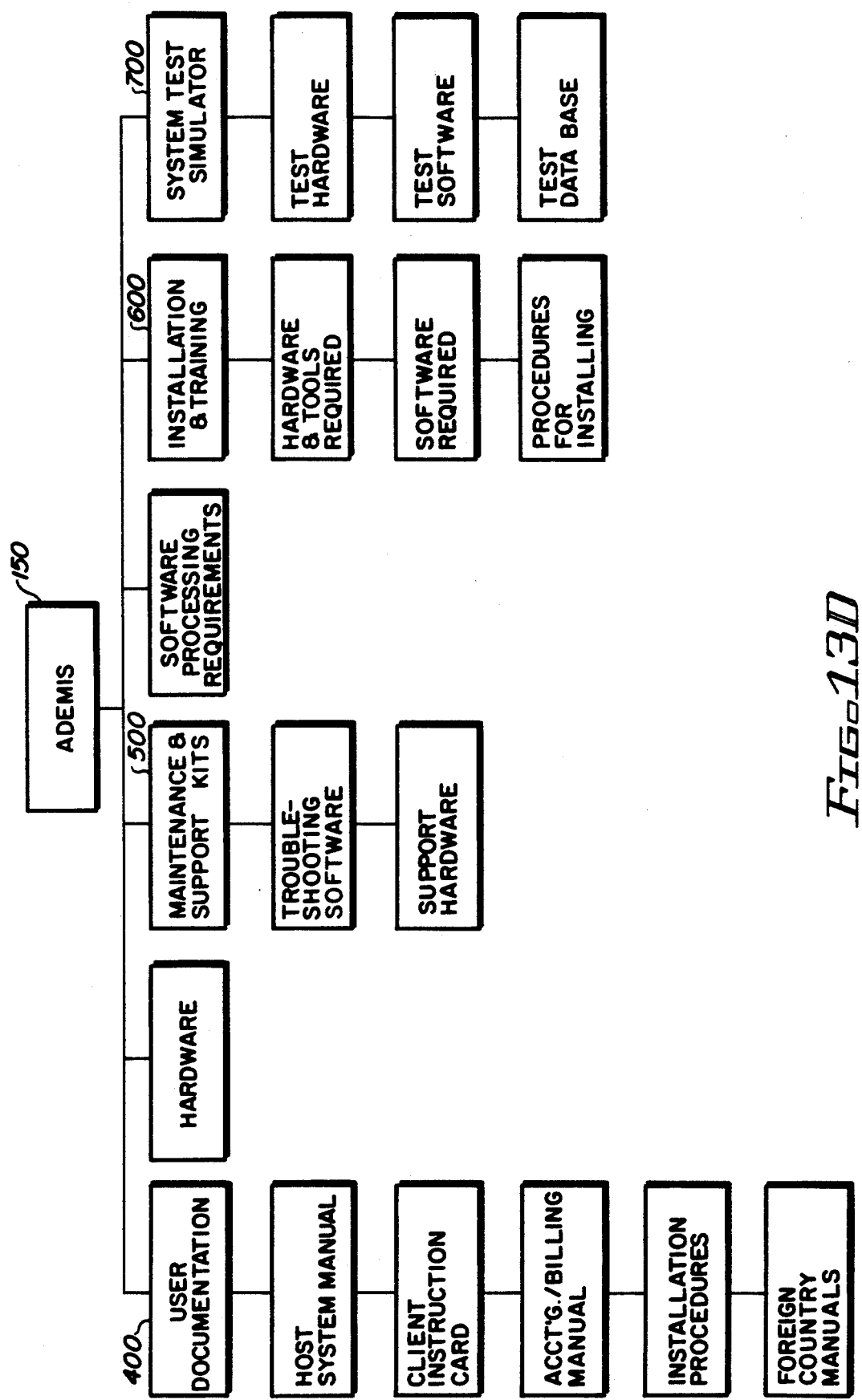

ADAPTABLE ELECTRIC MONITORING AND IDENTIFICATION SYSTEM

This application is a continuation-in-part of application Ser. No. 07/237,860; filed Aug. 29, 1988 now U.S. Pat. No. 4,952,928.

BACKGROUND OF THE INVENTION

The present invention relates to personnel identification and monitoring systems. More particularly, the present invention relates to an ADaptable Electronic Monitoring and Identification System (hereafter "ADEMIS") comprised of a variety of hardware and software modules. Advantageously, such an approach provides a great deal of flexibility in configuring a desired system that addresses the particular needs of a given application, such as the needs of the correction industry (prisons, jails, and other correctional and/or supervisory institutions). However, as well be evident from the description that follows, the flexibility provided by the present invention also makes it well suited for use in applications other than the corrections, such as medical, home health care, security and similar systems where individuals or objects need to be monitored and supervised.

Personnel monitoring systems used by law enforcement or other supervisory agencies, such as hospitals, are known in the art. Heretofore, however, such systems have been limited to monitoring the location of a designated individual, usually for the purpose of physically confining the individual to a designated area, such as a prison or jail; or such systems have monitored a particular medical parameter, such as heart rate, of an individual at a known location.

Since early times, most civilizations and societies have found it necessary to confine certain individuals, typically those found guilty of committing various crimes, to a prescribed area. The earliest monitoring systems were simply a cage or building in which the individual was placed, and around which guards were posted to physically watch the individual to make sure that he or she did not escape. Most of the jails and prisons used today are simply an extension of such practice.

In recent years, however, with the overcrowding of prisons and jails, and with the increased cost of constructing and staffing new prisons and jails, alternatives to physical confinement have been sought. One such alternative has been an electronic surveillance system which electronically determines whether a tagged individual remains within a prescribed area that is monitored with sophisticated electronic surveillance equipment. Schwitzgebel, et al, U.S. Pat. No. 3,478,344, is an example of an early attempt at such an electronic monitoring system for keeping track of the location of prisoners within a specified boundary. This is accomplished through the use of portable battery-powered RF transmitters, mounted on the wrist of the prisoner being monitored, and an array of directional antennas positioned around the boundary area. These antennas are able to determine the location of a transmitter (and hence the location of the prisoner wearing the transmitter) with respect to the antenna array. Thus, trained guards operating the antenna array and associated electronic equipment can keep track of the location of specific prisoners within the boundary area. Such a system thus attempts to replace the physical walls and fences of a prison with electronic walls and fences. Unfortunately, the system disclosed by Schwitzgebel does little, if anything, to physically prevent the individual from leaving the electronically confined area, other than to alert the guards of an exit from the area. Thus, the guards are not replaced by the system, merely aided by it; and the overall cost of constructing and operating such a monitoring system, as compared to the cost of constructing and operating a conventional prison, is not much improved.

More recently, a "house arrest" system has been developed and used by many law enforcement agencies to enforce parole requirements or to impose "house arrest". A paroled individual is typically required to remain in a prescribed geographical area, e.g. within a given city, for a set time and to regularly report to his parole officer. An individual placed under house arrest is typically required to remain at a specific location, often his own house or building, for a prescribed period of time. A "house arrest" system advantageously allows both functions to be readily performed.

The house arrest system of the prior art includes an electronic ankle tag that is unobtrusively fitted on the individual to be monitored. The tag includes a transmitter that periodically, or upon receipt of an interrogation signal, transmits an identification code over a short distance. Such tag may also include anti-tamper features that protect its electronic circuits from being altered, and that detect any attempts to remove the tag. The house arrest system may also include a field monitoring device, or FMD, that is placed at the location where the individual is to be confined, or the location to where the individual is to report on a regular basis, such as his or her home. The FMD, or equivalent device, receives the signal(s) transmitted from the tag(s) and keeps track of which signals were received when. (It is noted that the FMD may receive signals from more than one tag if a plurality of individuals wearing such tags are present within the location being monitored.) Periodically, e.g. three or four times a day, the FMD makes contact with a central computer, typically via a telephone line, and reports which signals were received and the time they were received. The report also includes any status information, such as any detected attempts to tamper with the tag or the FMD. Because each signal is uniquely encoded for a specific individual, the central computer combines the information contained in the reports received from all the FMD's located throughout the city in order to provide a comprehensive report on the whereabouts of each monitored individual at various times throughout a given day. Such comprehensive report can thus verify that a paroled individual has "checked in" at a specific location (i.e., been in electronic contact with a particular FMD) at a specified time; and can also verify that an individual under house arrest has remained at a specific location.

A house arrest system of the type described above is marketed by B.I. Inc, of Boulder, Colo., USA, under the name Home Escort System.

However, even the current Home Escort System marketed by B.I. Inc., as significant of an advance in the art as it represents, fails to provide more than location information about the tagged individuals. It is not uncommon for the court or supervisory agency to require, in addition to, or in place of, restrictions on physical movement, other restrictions, such as abstinence from drugs or alcohol. Hence, there is a need in the art for a personnel monitoring system that not only provides location information about supervised individuals, but that also selectively provides status and compliance information concerning such individuals, such as whether such individuals are refraining from consumption of alcohol and drugs.

It is also known in the electronic monitoring art to monitor the medical condition of a patient so that appropriate medical personnel can be alerted immediately in the event of a medical emergency, such as a heart attack. Mandel, U.S. Pat. No. 3,898,989, is an example of such a system. In Mandel, critical body functions are monitored through the use of special sensors placed on the individual which are coupled to a special transponder unit worn by the patient. The transponder unit is triggered by an interrogating signal, whereupon the information sensed by the sensors is transmitted in real time to a receiver. In this way the receiver is able to remotely monitor certain body functions, but no location information is included. Further, only critical and easily sensed body functions are monitored, such as heart rate and respiration rate. There is no suggestion that other body functions, such as those that might indicate consumption of drugs or alcohol, be monitored, and there is no suggestion that such monitoring be done for any purpose other than providing aid for a dangerous medical condition.

A further shortcoming of prior art electronic monitoring devices relates to their fixed configuration, resulting in inflexibility in their use and applications. Each system is typically designed for a specific monitoring purpose, and is accordingly configured for that specific monitoring purpose. Any modifications or changes that are desired or needed within the system often result in a complete redesign of the system, thereby providing yet another expensive inflexible system that meets the needs of just one application. This inflexibility can especially be a problem where several different governmental or supervisory agencies are involved, each having its own unique set of requirements relating to what must be monitored and how it must be reported. Hence, there is a need in the art for a flexible electronic monitoring system that can be readily and inexpensively adapted to suit the monitoring and reporting needs of a specific supervisory agency.

The above and other needs of the art are addressed and satisfied by the adaptable electronic monitoring and identification system described herein.

SUMMARY OF THE INVENTION

The present invention provides a low-cost, flexible, reliable, electronic personnel identification and monitoring system that comprises a collection of electronic and software modules and associated computer hardware. The system advantageously is configured to best fit the needs of a particular monitoring or identification application by merely selecting the appropriate modules that need to be a part of the system for the particular application at hand. When the appropriate modules and related hardware are thus selected and combined, a versatile monitoring and identification system is provided that can be used by law enforcement agencies, or other supervisory agencies, charged with the task of remotely and unobtrusively monitoring the location, condition, and activities of a large number of ambulatory individuals located within a relatively large geographic area. Such area may include an entire city, county, state, or other governmental jurisdictional area. The system advantageously provides the flexibility to allow such monitoring to occur from a central location, or from several locations.

The present invention fills the void of prior art monitoring systems by providing flexibility in how the system is configured. No longer must an agency (user of the system) choose a monitoring system that is "too much" or "too little" for the application at hand. Rather, a system that "just fits" the immediate needs of the agency can be obtained by selectively incorporating into the system only those software and hardware modules and related equipment that are needed to support the monitoring task at hand. Further, as the monitoring and identification needs change, the system can be readily upgraded or expanded to meet those changing needs by merely adding or deleting modules (software and/or hardware). All modules of the system are fully compatible with each other, and thus there need never be any concern that portions of the system will become obsolete.

A significant advantage of the ADEMIS system described herein is the flexibility it provides to its user to allow different levels of security and monitoring, at different times during a monitoring schedule, so as to optimize the availability of a desired or needed performance level at a minimum cost. Thus, a user of the system, such as a governmental agency, can keep an offender out of prison for a longer period of time for less cost based on a progression of monitoring levels.

Another significant feature of the adaptable electronic monitoring and identification system of the present invention is that it can be selectively configured in a way that not only monitors and identifies location, which remains an important variable to monitor, but also selectively monitors other prescribed information about the individual(s) being monitored. Such "other prescribed information" relates to whether the individual is complying with mandated restrictions or activities, such as might be ordered by a court of law, a physician, or other supervisory person or agency. For example, restrictions that might be imposed relate to abstinence from drugs, alcohol, or other controlled substances that are illegal or that might cause life-threatening behavior. Activities that might be monitored, either to determine their occurrence or non-occurrence, relate to maintaining a minimum level of exercise and personal hygiene, excessive regurgitation (as might occur, for example, for someone suffering from an eating disorder, such as bulimia), appropriate sleeping or resting periods, episodes of violence (such as might occur during spouse or child abuse), or the like. Advantageously, the present invention provides a system whereby all such restricted or mandated activities can be selectively monitored in an unobtrusive and inexpensive manner from a central location, or from several remote locations in communication with a central location.

One embodiment of the monitoring system herein described includes the basic elements of the location-determining monitoring systems of the prior art, i.e.: a tag or transmitting unit that is worn or carried by the individual being monitored, and that periodically transmits a uniquely encoded signal that serves to identify the person being monitored; a field monitoring unit, or FMD, that is selectively positioned near the person being monitored (or at the location where the person being monitored should be found) to receive the signals transmitted from the tag or transmitting unit; and a central processing unit, or CPU (sometimes referred to as a "host" CPU), that automatically or by request receives information from the FMD from which desired compliance and non-compliance reports are generated.

Unlike the prior art systems, however, the transmitting tag of this embodiment of the invention may be selectively configured to assume a transponder mode of operation wherein it transmits its identifying signal only upon receipt of a request signal from the FMD. The FMD, in turn, may be configured as a "dumb" device in that it need only relay signals (after amplification and buffering) between the tag and the host CPU. When thus configured, all of the intelligence of the system resides at the host CPU, and the host CpU determines the appropriate time to request the FMD to request a signal from the tag, which signal (after receipt by the tag) is immediately transferred on to the host CPU for logging and processing. Alternatively, and as described in the prior art, the FMD can be selectively configured as a "smart" device, in that it can perform many of the requesting, processing and logging tasks that would otherwise have to be performed by the host CPU.

Further unlike the prior art systems, this embodiment of the invention selectively includes appropriate sensors or electrodes that are incorporated within or otherwise coupled to the transmitting/transponder tag. These sensors monitor selected body functions or parameters, such as heart rate, temperature, ankle diameter, posture, amount of skin perspiration, muscle movement (activity), and the like, and provide the sensed information to the transmitting circuits of the tag. There, this information is appropriately included within the identifying signal that is periodically transmitted by the tag unit. The FMD receives this information, and, if configured as a "smart" device, logs it, compiles it, and forwards it on to the CPU at the appropriate time or upon request. (If the FMD is configured as a "dumb" device, this information is only obtained from the tag upon request by the CPU, and the information is immediately passed on to the CPU.) The CPU, in turn, processes the information in order to interpret it and to provide to the user of the system an indication of the location, condition, and activities of the monitored individual. Further, if desired, the host CPU produces written reports that identify the compliance or non-compliance of each monitored individual with the imposed restrictions..

Still further unlike the prior art, the transmitting/transponder tag used within the monitoring system of this embodiment of the invention provides various options that can be readily selected at the factory in order to allow an otherwise "standard" transmitting tag to be used for different monitoring applications. One such option, as already discussed, relates to whether the tag operates in a transmitting mode (periodically, e.g. every 90–120 seconds, the tag transmits an identification signal, modulated with other sensed information) or a transponder mode (transmits its identification signal, modulated with other sensed information, only upon receipt of a request from the FMD). Similarly, different modules or function packs may be easily inserted into a "standard" FMD, at the factory and/or at the time of installation, in order to "customize" the FMD for a particular monitoring application. Likewise, different application programs may be readily selected or loaded into the host CPU, or other CPU's coupled to the host CPU, in order to direct the CPU(s) as it interprets the data received from the various FMD's, each of which may be monitoring individuals for a different application, and prepares the various reports needed by the different supervisory agencies having an interest in the individual being monitored.

A further embodiment of the invention provides administrative case load management capability for allowing an agency's host computer to automatically perform the "back end" monitoring of low risk personnel who are required to make periodic, e.g., weekly, monthly, or yearly, contact with the agency to keep the agency advised of the status of such persons.

Accordingly, it is a feature of the present invention to provide a personnel monitoring system that provides the users of such system with a great deal of flexibility in how a basic monitoring system is configured in order to monitor a wide variety of activities. Such flexibility is realized by constructing the system from modules of hardware and software elements that are combined together in order to fit the application need at hand.

It is another feature of the invention to provide such a flexible modular system that can be easily upgraded from one configuration to another.

It is a further feature of the present invention to provide such a flexible monitoring system that measures the compliance or non-compliance of the monitored individual against a prescribed performance or behavior standard.

A still further feature of the present invention is to provide such a flexible monitoring system that includes the ability to monitor the location and/or activities and condition of the individual being monitored as a function of time, thereby advantageously allowing a determination to be made as to the relative time periods during which compliance or non-compliance of a prescribed standard has occurred.

Yet another feature of the present invention is to make the flexible monitoring system herein described available at a reasonable cost, thereby allowing supervisory agencies to better meet their stewardship obligations of monitoring and watching over those individuals charged to their care.

BRIEF DESCRIPTION OF THE DRAWINGS

The above and other features and advantages of the present invention will be more apparent from the following more particular description thereof presented in conjunction with the following drawings wherein:

FIG. 6 is a block diagram of one configuration of the electronic elements and circuits contained within the FMD;

FIG. 7 identifies the various software submodules that may be used within the host CPU;

FIG. 9 is a Table showing, in general, how various body parameters are affected by engaging in certain activities;

FIGS. 10A and 10B depict one technique that is used to measure the amount of swelling of the leg or ankle;

FIGS. 11A and 11B illustrate two respective circuits used with a piezoelectric element, either one of which may be used to sense a desired function, such as pulse rate or activity;

FIG. 12 shows one approach of using two tags on the same individual for the purpose of sensing various physiological parameters, such as heart rate;

FIG. 13A is an organizational chart for a particular monitoring system built in accordance with the present invention, illustrating the various categories of subsystems and submodules that are included therein;

FIG. 13D is a chart of the system of FIG. 13A detailing the user documentation, maintenance and support, installation and training, and system test simulator requirements thereof; and FIG. 14 is a block diagram of the hardware components of a "programmed contact" embodiment of the present invention.

DETAILED DESCRIPTION OF THE INVENTION

The following description presents the best contemplated mode for practicing the invention. This description is not to be taken in a limiting sense but is made merely for the purpose of describing the general principles of the invention. The scope of the invention should be ascertained with reference to the appended claims.

The present invention will now be described. This description is best understood with reference to the drawings, wherein like numerals are used to represent like parts or elements throughout.

Figure 1:
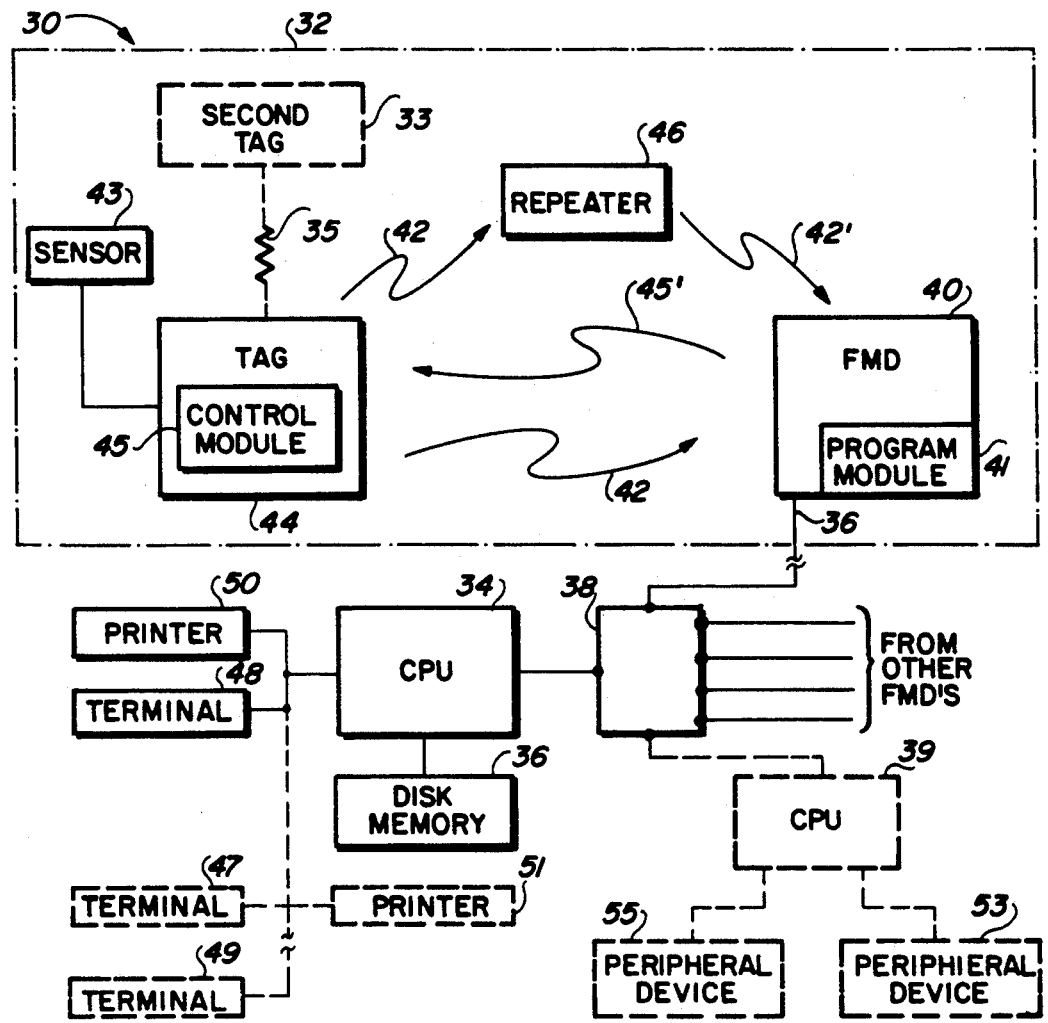
FIG. 1 is a block diagram of the basic hardware elements associated with the personnel monitoring system of the present invention.

Referring first to FIG. 1, there is shown a block diagram of the basic hardware used in a personnel monitoring system 30 in accordance with the present invention. The system 30 includes one or more remote monitoring areas 32 and at least one central processing unit (CPU) 34. The CPU 34 is coupled to the remote monitoring area 32, in accordance with the embodiment shown, by way of a telephone line 36. One or more conventional telephone switching stations 38 couple the telephone line 36 to the CPU 34.

Within each remote area 32, which area 32 may be a house or other conventional building, there is included at least one field monitoring device (FMD) 40. The FMD 40 receives signals (represented as wavy arrows 42 in FIG. 1) from a transmitting tag unit 44. Depending upon the configuration selected, these signals may be transmitted periodically by the tag unit 44, e.g., every 90–120 seconds, or they may be sent only in response to a request signal 45' received from the FMD 40. These signals 42 contain information that uniquely identifies the tag 44 from which the signal originates, and that indicates the status of the circuits internal to the tag, including whether such circuits have sensed an attempt to remove the tag. Further, the tag may be selectively configured to include one or more sensors 43 that sense prescribed conditions associated with an individual on whom the tag is placed. For example, one application of the monitoring system may require that the pulse rate and amount of perspiration of the individual be monitored so that a determination can be made as to whether such individual is taking drugs (in which event these monitored rates would change in a quite predictable fashion). The signals 42 transmitted from the tag 44 advantageously contain information about the condition sensed by the sensor(s) 43 relating to these or other parameters, in addition to the identification and status information referred to above.

Depending upon the particular characteristics of the remote monitoring area 32, the monitoring system may also include a repeater circuit 46 that can be selectively positioned within the area 32. The purpose of the repeater circuit 46 is to receive the signals 42 from the tag 44 and to retransmit these signals, after a short delay, to the FMD 40 in order to eliminate dead spots. Such retransmitted signals are identified in FIG. 1 as signals 42'.

It is noted that more than one FMD 40 may be located within the remote monitoring area 32, thereby eliminating the need to install the repeater 46. For example, one embodiment contemplates that there will be one FMD for every telephone within the area 32. Most of these telephones (assuming there is more than one) will likely share the same telephone number. However, each FMD will have a unique identification number or code associated therewith. Thus, while the host CPU 34 will, in effect, have all such FMD's on the line at the same time once it calls the telephone number associated with the area 32, it can still "talk" to just one FMD at a time by identifying such FMD using its unique code.

Still referring to FIG. 1, only one tag 44 is shown within the remote monitoring area 32. However, the system of the invention contemplates that a plurality of tags 44 positioned within the monitoring area 32 could be monitored by the same FMD 40 (or collection of FMD's), with each tag generating its own unique signals at periodic intervals or upon request.

Further, it is noted that some configurations of the invention may require the use of a second tag 33 fastened to the same individual as in the primary tag 44. As will be explained hereinafter, one such tag can be fastened to the wrist, for example, and the other tag can be fastened to the ankle. The main purpose of this second tag 33 is to assist the primary tag 44 as it monitors certain body parameters. For example, the body of the individual, for electrical purposes, may be considered as a resistance 35. Changes or variations in this resistance can be measured between the tag 44 and the tag 33 in order to determine certain physiological parameters, such as heart rate, respiration rate, muscle tissue activity (muscle stretching and contracting), and the like.

Advantageously, the CPU 34 can be coupled through the telephone communication link, or other appropriate communication links, to a large number of remote monitoring areas. Typically, the CPU 34 will randomly or sequentially poll each of the remote monitoring areas with which it can establish a communication link. Once a communication link is established, all of the data stored within the FMD 40 since being last polled (assuming a "smart" FMD is configured) can be transferred to the CPU 34. Alternatively (assuming a "dumb" FMD is configured), the FMD can initiate request signal 45, and wait to receive the signal 42 that is generated by the tag in response to such request signal. The received signal 42 can then be transferred directly to the CPU. In either event, all of the information contained in each identification signal 42 can eventually be transferred to the CPU 34, at which location it is interpreted and processed so that meaningful reports can be generated indicating the location, condition, and activities of a particular individual carrying a known tag 44.

The hardware associated with the CPU 43 can be selectively configured to meet the needs of the particular user or agency of the system. Typically, at least a printer 50 and a terminal 48 (which includes a keyboard or equivalent) are coupled to the CPU 34 in order to monitor and alter, as required, the CPU operation as it carries out its function of gathering and interpreting data from the various remote FMD locations. Additional peripheral devices, such as a disk storage memory 35, or equivalent, may also be coupled to the CPU 34. Further, additional terminals or microcomputers 47 and 49, and an additional printer 51, may all be coupled to the CPU 34 in order to form a local area network, each terminal having access to all of the data held in the CPU 34. Typically, such terminals 47 and 49 will be "smart" terminals, or equivalent (such as personal computers) and each terminal would thus be able to generate its own unique reports based on the data made available by the CPU 34.

Further, in some configurations, it is possible to couple CPU 34 with a second CPU 39 via an appropriate communication link, such as a telephone line. Additional peripheral devices 53 and 55, associated with CPU 39, could thus provide additional flexibility in how the system is utilized. Moreover, in addition to coupling the two CPU's together, CPU 39 could independently access the FMD 40, or other FMD's, in order to collect desired data from the various remote areas where the tags are located. Thus, for example, CPU 34 could be maintained and operated by a first agency, such as the Parole Department of the State Correction's Agency; and CPU 39 could be maintained and operated by a second agency, such as a local Police Department. The two CPU's could thus operate independently, if desired, or they could be programmed to communicate with each other on a periodic basis in order to verify and/or share the data collected from the various remote areas 32, and to flag any discrepancies found in such data.

Still referring to FIG. 1, the tag 44 includes a control module 45, installed at the manufacturing facility, that adapts or controls the basic circuits of the tag so that a desired monitoring function may be carried out. For example, some applications may require that the anti-tamper circuits of the tag be enabled, while other applications may not. Similarly, some applications may require the use of two or three sensors, all of which may be incorporated into the housing of the tag 44, while other applications may require the use of only one sensor. The control module 45 can quickly configure the tag to the needed configuration. For some applications, the control module 45 may be realized with simply a jumper plug that interconnects certain control terminals and disconnects others. For other applications, the control module 44 may require the addition of read only memory (ROM) and some limited random access memory (RAM), as well as some very simple processing circuitry (such as a clock), in order to properly interface with the various sensors 43 that are needed for that particular application. However, for the most part, the basic circuits of the tag 44 are the same regardless of the application, thereby allowing the tag to be manufactured in a uniform, consistent, cost-effective manner. Enhancements to the tag can then be made by adding a selected module or modules thereto as required.

Similarly, the FMD 40, which is a microprocessor-based device, or equivalent (such as a custom LSI chip), includes therein a program module 41 wherein the program that controls the device is loaded. This program module 41 is typically realized with a ROM pack that has been programmed at the manufacturing facility for a particular application. Advantageously, several ROM packs can be preprogrammed at the factory, each for a particular application, and the needed ROM pack can be easily installed in the FMD during the installation process of the FMD at the remote area location. Alternatively, the ROM pack or program module 41 can be installed during manufacture of the FMD. Either way, the manufacture of the FMD, for all applications, is reduced to a consistent, controlled, cost-effective approach.

Referring next to FIG. 14, a block diagram of a "programmed contact" embodiment of the present invention is depicted. This embodiment may be used for applications where the individual being monitored must "report in" at prescribed times. Further, the embodiment contemplates that the tag 44' need not be worn by the individual (although for some applications it may be worn). Rather, it need only be carried by the individual, much as a credit card or identification badge, and presented to an FMD at a designated location at a prescribed time. According to this embodiment, the tag 44' generates its identification signal 42 only in response to a trigger signal 45' generated by the FMD 40'. Typically, such a signal is generated when a manual switch 144 on or near the FMD 40' is activated by the user of the tag. (Such a switch may be activated automatically when the tag 44' is placed within a holding receptacle or cradle 146.) The activation of the switch 144 could also optionally activate other identification devices coupled to the FMD, such as a video camera 148. The video signal could then be transferred to the CPU location, through the same communication link established by the FMD, where it could be used to further identify the individual. In addition, appropriate biometric sensors 43' included within the tag 44', or other biometric sensors 150 coupled to the FMD 40', could electronically or otherwise detect other identifying parameters associated with the individual, or the biomedical condition of the individual. Signals representative of the detection(s) thus made could also be sent to the CPU, where such signals could be used to positively identify to the CPU that a designated individual—the one to whom the tag 44' was assigned—appeared at the FMD 40' from which the signal originated at the time the signal originated. (Alternatively, the FMD 40' could time-log the signal(s) received from the tag 44' or the video camera 148 or the sensors 43' and 150, store these signals, and send them on to the CPU at a later time, including the time at which the signals were received.) Further, the biomedical condition of the individual at the time of the appearance before the FMD 40', as detected by the biometric sensors 43' and 150) could be included in the signals sent to the CPU. Parameters that could optionally be included for sensing by the biometric sensors 43' and/or 150 include voice, fingerprints, breath analysis, and the like.

Figure 2A:
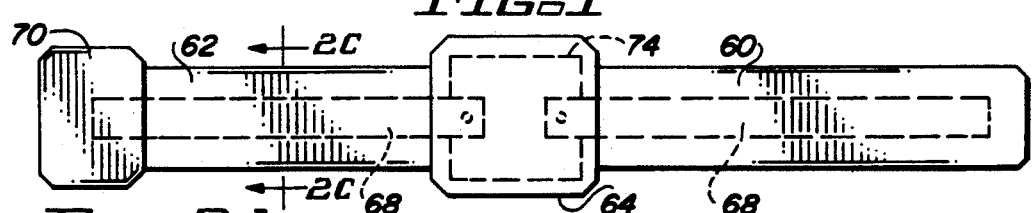
FIG. 2A is a top X-ray view of a wrist embodiment of the transmitting/transponder tag of the present invention.
Figure 2B:
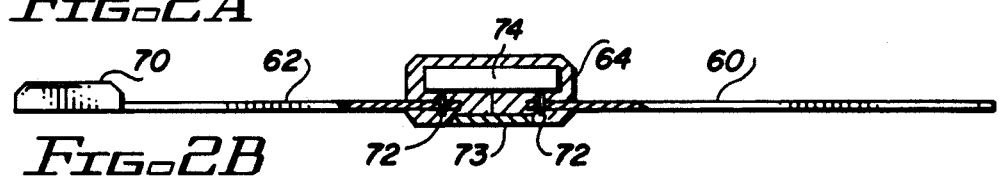
FIG. 2B is a side sectional view of the wrist embodiment of FIG. 2A.
Figure 2C:
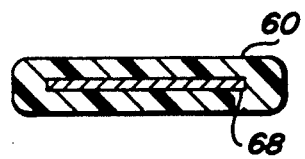
FIG. 2C is a cross-sectional view of the band of FIG. 2A taken along the line 2C—2C.

Referring now to FIGS. 2A, 2B, and 2C, there is shown a top, side, and sectional view, respectively, of a tag embodiment adapted to be worn on the wrist of the individual being monitored. Straps 60 and 62 are connected to a main body 64 wherein the electronic circuits 74 and battery 76 of the tag are housed. Embedded within the straps 60 and 62 is a conductive strip 68. A fastener 70, attached to one end of strip 62, allows the other end of strip 60 to be non-removably attached thereto. In this respect, the straps and fastener of the wrist embodiment shown in FIG. 2 are much like a typical hospital identification bracelet that is issued to all patients upon admission. Once fastened, the only way to remove the device is to cut the strap.

The conductor 68 is preferably a simple flat conductor running through the wrist strap that will detect a tamper condition if the strap is cut or shorted. This configuration is made, in accordance with the preferred embodiment, by placing a thin conductive strip on the inside of double laminated plastic. Alternatively, the conductor 68 may be made from an inner layer of conductive plastic material or a painted on conductive material. The conductors do not need to make electrical contact with each other at the fastener end when the strap is fastened on the wrist. All that need occur is for the conductive strap 68 to create a capacitor at the strap connection that enables an AC signal to pass through to the other side. Using this approach, either a cut or a short can be readily detected. Electrical contact is made between the conductive strip 68 and the electrical circuits 74 by poking a sharp pin 72 through the strap at the time the strap is connected to the housing 64. Advantageously, the strap can be inexpensively manufactured as a separate item and sold to the user as a throwaway part. At least one electrode 73 forms part of the underside of the housing 64. This electrode is in electrical contact with the circuits 74 of the tag, and is in contact with the skin of the wearer once the tag is fastened. This electrode forms part of the sensor 43 used to sense or measure specific body parameters.

Figure 3:
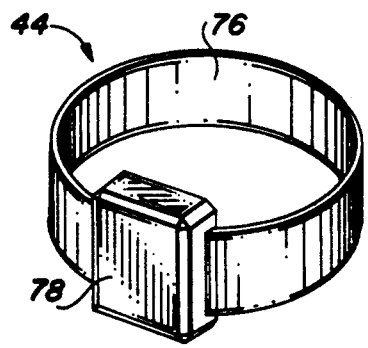
FIG. 3 is a perspective view of an ankle embodiment of the transmitting/transponder tag of the present invention.

FIG. 3 shows a perspective view of a tag 44 that is adapted to be fastened to the leg (ankle) of the user. The tag 44 of FIG. 3 is shown with its strap 76 in its fastened position. Once so fastened, special tooling is required in order to unfasten the strap. A housing 78, inside of which the electrical circuits and components of the tag are housed, is contoured to fit the curvature of the ankle, thereby allowing a comfortable fit between the tag and the leg. It is noted that many of the features of the wrist embodiment described above in connection with FIG. 2 may also be incorporated into the ankle embodiment of FIG. 3.

Figure 4B:
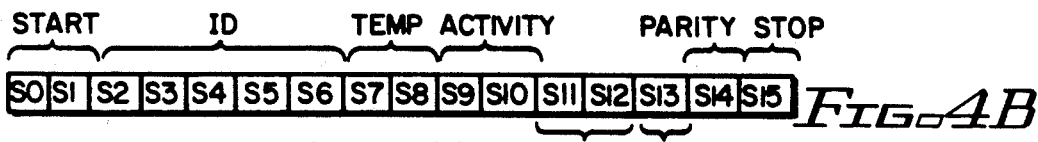
FIG. 4B is a representation of the bit pattern that may be used within the signal 42 generated by the transmitting/transponder tag.
Figure 4A:
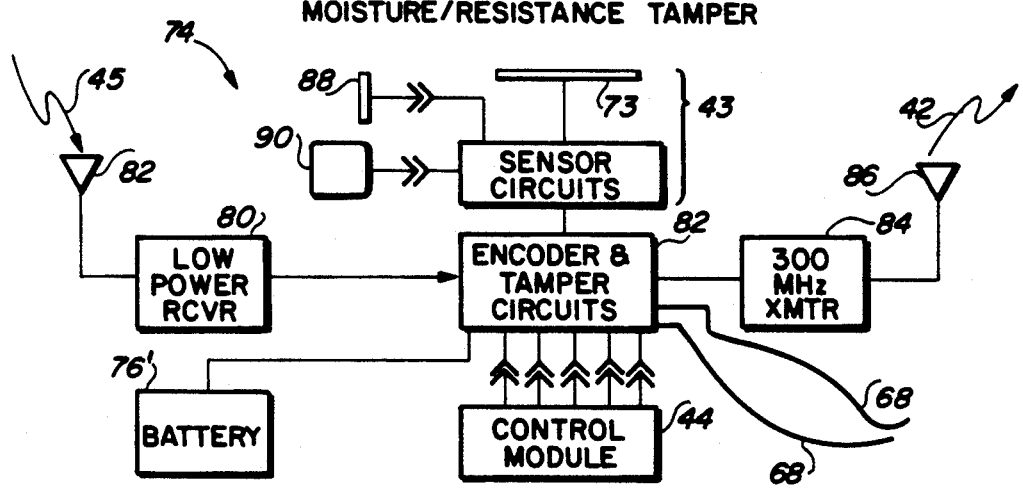
FIG. 4A is a block diagram of one embodiment of the electronic elements and circuits contained within the tag of the present invention.

FIG. 4A depicts a block diagram of the electrical circuits 74 of the tag 44 in accordance with one embodiment of the invention. A battery 76' provides power for the device. A control module 44 plugs into the unit during its manufacture and determines the configuration that the tag will assume. In one configuration, a very low power receiver circuit 80 is enabled to receive an interrogate signal 45 from the FMD 40. In response to receipt of this signal, the encoder and tamper circuits 82 generate a digital word signal that is passed to a transmitter circuit 84. The transmitter circuit 84 then generates the signal 42 (described in connection with FIG. 1) that is transmitted back to the FMD through antenna 86. In a second configuration, a clock circuit included within or enabled by the control module 44 causes the signal 42 to be periodically generated, e.g., every 90–120 seconds. The repetition rate at which the signal is generated can be selected through the control module, and can selectively be made either shorter or longer than the 90–120 second repetition rate stated, depending upon the particular application. The exact repetition rate is not viewed as critical, and can vary over a wide tolerance without impairing the performance of the tag.

As previously indicated, one or more sensors or electrodes 43 are also incorporated into the tag unit 44. The tamper logic that senses the capacitive coupling associated with the conductive strips 68 of the strap 60, 62 (wrist) or 76 (ankle) is properly considered part of the sensor circuits. For some applications, this tamper sensor may be the only sensor that is enabled. However, still other applications may not require a tamper sensor, in which case even this sensor may be disabled. Other sensors that are contemplated as being included in the tag 44 include an electrode 73, a temperature sensor 88, and an activity sensor 90. All of these sensors interface with the main logic circuits 82 of the tag through appropriate sensor circuits 92, the function of which circuits is primarily to provide a suitable interface between the sensor elements and the digital logic circuits.

The electrode 73 may be used as one of the two points between which a body impedance measurement is made, as described previously in connection with FIG. 1. Alternatively, or conjunctively, the electrode may be used to sense the amount of moisture (perspiration) on the skin; and may even be used in conjunction with other sensors in order to analyze the content of such moisture. The use of skin electrodes, such as electrode 73, is well known in the art and will not be further described herein.

The temperature sensor 88 is preferably an integral part of the housing 64 or 78 of the tag, and is positioned so as to sense skin temperature. Temperature sensors are well documented in the art, and accordingly no further details will be provided herein other than to indicate that temperature sensing within the tag is preferably done on a sampled basis, thereby preserving power.

The activity sensor 90 may be either a piezo-electric element, or a mercury switch, or a combination of the two. A piezo-electric element, as is well known in the art, generates an analog electrical signal having a frequency and amplitude that varies as a function of the intensity of the mechanical forces to which the element is subjected. In recent years, such piezo elements have successfully been incorporated into implantable pacemakers, as detailed for example in U.S. Pat. Nos. 4,140,132 and 4,428,378, issued to Dahl and Anderson, respectively. The present invention recognizes that similar techniques as are described in the Dahl and/or Anderson patents can be used to incorporate a piezo element in a tag unit 44 of the present invention.

A mercury switch is a switch similar to those used in thermostats to sense a temperature change. The switch simply consists of a bead of mercury within an evacuated tube having electrodes at the ends thereof and/or positioned along the length thereof. As the device is subjected to physical forces, the mercury bead moves within the tube, thereby making and breaking electrical contact between the electrodes. Hence, by monitoring a pair of such electrodes, a determination can be made as to the relative intensity of the physical forces that are applied to the device. Further, such a device can detect relative position, as a level, because the mercury bead will always assume a given orientation with respect to the gravitational field. Accordingly, the device can easily determine if the individual carrying the tag has assumed a standing up (vertical) position or a lying down (horizontal) position. Further, without too much difficulty, the sensor could determine if the vertical position were stable or unstable.

In order to provide as much flexibility within the tag as possible, yet in order to keep the circuitry within the tag as simple as possible, it is contemplated that the signal 42 transmitted to the FMD 40 will include, in addition to the identification bits that identify the source of the signal, appropriate sensor bits that indicate if a corresponding sensor has sensed a parameter exceeding a prescribed threshold. After each signal 42 is generated (whether by request or periodically), the latches (within the encoder and tamper logic 82) that define the states of these bits will be cleared. Thus, the CPU, by monitoring these bits each time a signal (or combination of signals) is received from the FMD, can determine whether certain conditions have occurred, and if so, whether such conditions have occurred more than once.

Alternatively, the absolute value of the signals obtained from the sensors can be included in the signal 42 as a two or three bit value. These values can then be decoded at the CPU in order to provide a relative indication of how a particular parameter has varied since the last signal was received. The manner of using sensors to accurately detect physiological parameters is well known in the medical art. Such techniques can be readily applied to the monitoring system herein described by those skilled in the art.

Referring briefly to FIG. 4B, a representation of the signal 42 (prior to modulating an RF carrier signal) is shown. The signal comprises 16 bits, S0–S15. Bits S0 and S1 are used as start bits. Bits S2–S6 are identification bits that uniquely identity the tag (and hence the individual wearing the tag). Bits S7–S8 are used to signal the sensed temperature; bits S9–S10 signal the level of sensed activity; bits S11–S12 signal the sensed moisture and/or resistance; bit S13 signals the tamper condition; bit S14 is a parity bit; and bit S15 is a stop bit. Other patterns of bit assignments could, of course, be used. Further, the length of the bit word could be shortened or lengthened, depending upon how much information needs to be transferred.

Figure 5:
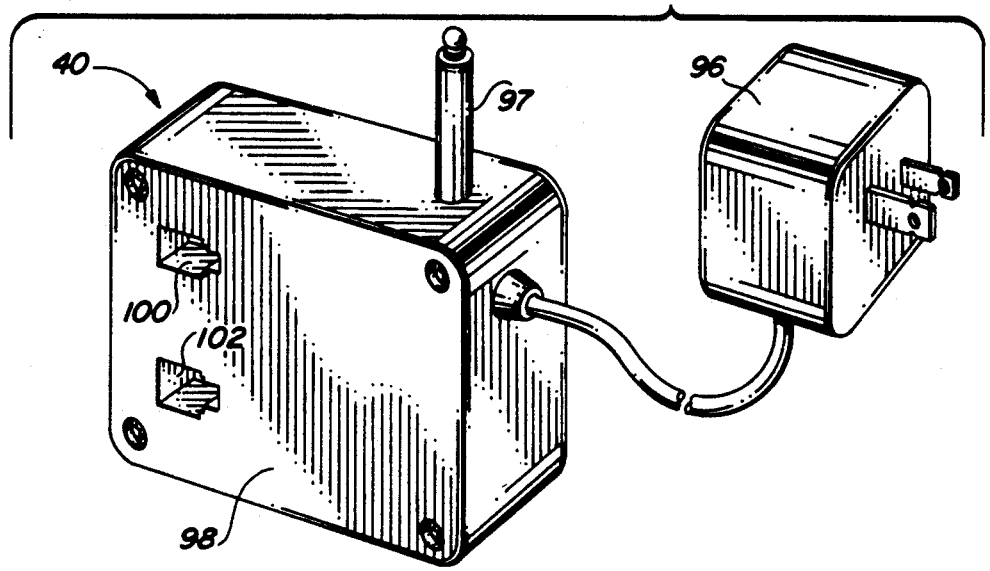
FIG. 5 is a perspective view of one embodiment of the FMD.

Referring next to FIGS. 5 and 6, a perspective view and block diagram of a simplified embodiment of the FMD 40 is illustrated. This simplified embodiment can be used where the particular monitoring application does not require extensive intelligence or back-up circuitry at the remote area 32. The unit is simplified to save cost and to facilitate manufacture. It is still a microprocessor-based device having a simple microprocessor circuit 91 therein (although it is contemplated that the logic functions performed by the microprocessor circuit could eventually be built for less expense using custom LSI or MSI circuits). However, it has little if any memory capability. The basic components used in the simplified FMD include a simple RF transmitter 92, an RF receiver 94, a small but efficient antenna 97 for the appropriate RF frequency range, a wall transformer unit 96, and a low cost plastic case 98. A pair of standard telephone quick disconnect terminals 100 and 102 provide for a quick easy connection with a standard telephone line 103 and telephone 104.

The FMD of FIGS. 5 and 6 is a "dumb" device that only interrogates the tag units 44 when the CPU 34 (or the CPU 39) on the other end of the telephone line (or other communication link) requests that such interrogation occur. Hence, the CPU 34 (or 39) at the agency site does all of the data management and processing, and the FMD 40 is just a conduit through which requests are passed to the tag units from the CPU, and data is passed to the CPU from the tag units. As shown in FIG. 6, the electronic circuits of this simplified FMD include a transmitter 92, a receiver 94, a power supply (wall transformer) 96, a modem 99, and some logic circuits 91 (typically realized with an inexpensive microprocessor circuit or equivalent). Further, there is some limited ROM memory 106 wherein a unique identification code is permanently stored. Also, additional ROM and some RAM, as required for the particular application, may be added to the device by means of a removable program module 41.

In operation, the simplified FMD 40 of FIGS. 5 and 6 is hooked up between the telephone line 103 and the telephone 104. This arrangement allows the unit to "steal" the first ring and look for a signal from the CPU. If there is no signal, the unit will allow subsequent rings to go through and operate the telephone in conventional manner. Such operation assumes, of course, that a telephone signal can be sent down the telephone line 103 while the telephone is ringing and still "on hook." If this cannot be done, then all telephone calls must be answered and tested to see if the call is for the FMD. If not, the FMD hangs up and does not answer the next call if it occurs within 60 seconds. Such logic, or equivalent logic, must be built-in to the particular program (e.g., the program module 41) used to control the microprocessor 91. If the call is answered by the FMD, and it is verified that the call is for the FMD from the CPU, the transmitter 92 and receiver 94 of the FMD are connected to the modem 99. The CPU then sends the proper digital codes to interrogate a tag. The tag responds by sending back its signal through the FMD to the CPU. The intelligence to do this whole operation resides in the CPU, not in the FMD.

The ideal range between the FMD and a tag unit 44 is around 50 feet. The minimum distance is around 10 feet, the typical distance from a wrist unit to the FMD while an individual is in bed.

As is evident from the above description of the simplified FMD, additional memory capacity and program capabilities can be readily added to the FMD by means of the program module 41. A desired program module 41 is optionally inserted into the simplified FMD at the manufacturing facility, or by authorized field personnel. Additional features that may be included within the FMD include the ability to store and log information received from the tag units, and to subsequently download such data to the CPU at the time of the next CPU telephone call. Further, the FMD can be configured to immediately initiate a telephone call to the FMD in the event a tamper condition is detected. The FMD itself is tamper protected by incorporating a suitable switch, such as a microswitch, inside of its case 98 that is automatically opened whenever the back of the case is removed. Additional, more sophisticated, tamper protection circuits can be incorporated into the FMD as the need arises. For example, FMD tamper circuits may detect power failures, attempts to unplug the telephone line, or physical movement of the FMD. Similarly, the FMD can be equipped with a battery backup power source so that in the event of a power failure, it can still operate and provide the necessary communication link between the host CPU and the tag device(s).

As is evident from the above description, the "dumb" FMD device can be made relatively "intelligent" through the addition of removable memory and programs contained within the program module 41. As more and more intelligence is added, the FMD device can therefore approach the sophistication of the FMD device described in U.S. patent application Ser. No. 852,831, which application is incorporated herein by reference. However, the preferred embodiment is to keep the FMD device simple so that its primary function is that of relaying commands and data between the tag unit and the host CPU. In this way, all of the "intelligence" can reside at the host CPU, where different programs and capabilities can readily be added or subtracted to the system by merely loading and operating different application programs.

The host CPU comprises CPU hardware and CPU software. The CPU hardware is preferably realized using a product family of commercially available CPU's, such as the IBM II line of personal computers, based on the 386 processor and using the OS/2 operating system. (Other CPU product lines, ranging from mini-computers to micro-computers, could, of course, also be used.) The CPU should be on the leading edge of technology in order to minimize the threat of obsolescence and to allow for an increase in performance by addressing additional memory, I/O ports, networking, peripherals, (hard disk drives, floppy disk drives, tape drives, printers, modems, etc.) and a multiuser/multitasking operating system.

The CPU software is advantageously categorized into several different submodules, or directories, as illustrated for example in FIG. 7. Not all possible software submodules are illustrated in FIG. 7; but sufficient are illustrated to teach the flexibility that is available to the system of the present invention. As shown in FIG. 7, at a first level, two basic country software modules are available: (1) United States, and (2) Foreign. (In this case, "Foreign" is a generic term that refers to software modules that will be available for each country, depending upon the needs and requirements of a particular country.)

Assuming that a United States submodule is selected, FIG. 7 shows that various "agency" software modules can be selected at a second level. For example, there may be a software module for the Federal Government, State Government, County Government, the Sheriff's Department, or Halfway Houses. If, for example, the "County" software module is of interest, FIG. 7 illustrates seven further software submodules that are available: (1) Probation; (2) Parolee; (3) Pretrial Bond; (4) Driving Under the Influence (DUI); (5) Work Release; (6) Juvenile Department; and (7) Institutions. While many of these submodules will share common characteristics, each has its own unique requirements sufficient to justify a separate software submodule.

The next level of software submodules identified in FIG. 7 relates to the different type of technologies that may be used to achieve the desired monitoring function. For example, in addition to the presence/absence type of monitoring that is done in the prior art using RF signals, the present invention contemplates, in addition to or in combination with presence or absence detection, alcohol detection, voice identification, or fingerprint identification. (It is noted that both voice identification and fingerprint identification can be achieved by matching a voice or fingerprint signal with a representative template signal that is stored in ROM memory.) Further, as indicated above, the tag of the present invention may be a transponder type of tag (as opposed to a transmitting type of tag), in which case a different software module will be required. Further, various tracking software modules may also be used to allow the system to track a tag wearer, either within an institution (as an RF transmitting tag comes within range of strategically placed FMD units throughout the institution), or throughout a much larger area, such as could be achieved with satellite tracking.

Finally, FIG. 7 depicts several optional or add-on types of software submodules that could be optionally included within the monitoring system of the present invention. These include a case management submodule (to aid in the management of a particular individual, including keeping historical data readily available); a graphics package and reports submodule; an accounting/billing submodule, a networking submodule to tie together multiple CPU's within a single agency; a networking submodule for use by multiple agencies; a networking submodule to tie together several terminals within a single institution with a single CPU; and an administration case load management submodule.

The administration case load management submodule is of particular note. This submodule allows the administrative agency to keep track of a large population of personnel who are on the "back end" of the agency's responsibility. Such personnel are considered very low risk, and are under obligation to contact the agency periodically, e.g. every week, every month, or every year, to advise the agency of their current status. Such personnel need not carry or wear a tag. All they need do is pick up a telephone or make a personal visit to their assigned agency officer. When contact is established with the agency, which will usually be by telephone (but it could also be a personal visit) the agency officer asks them certain basic questions, such as if their address is the same, if their employer is the same, and if they have been arrested for any reason during the past period since last contacting the agency. If there have been changes, the officer makes note of the same and updates their file.

At present, administration case load management is handled manually by each agency. This represents a significant burden for some agencies as the number of personnel on "back end" supervision can be quite large. For example, in Los Angeles County, Calif., it is estimated that there are over 80,000 persons on probation. Fifty-five percent of these persons (i.e., 44,000) are on "back end" supervision. On average, this population of supervised personnel must contact the agency once a month. Thus, there are some 44,000 phone calls (or other contact) that agency personnel must make each month in monitoring the status of this "back end" population.

The present invention advantageously allows back-end supervision to be performed automatically by the host computer using the administrative case load management software submodule. When this option is included in the system, a computer file is maintained for each of the monitored persons. This file contains the basic status information. The monitored person must make contact with the host computer at the regularly scheduled interval, e.g., once a week, once a month, or once a year. Such contact will typically be accomplished over a conventional telephone line, but it is understood that any telecommunicative contact, as that term is used herein, could be made. Typically, where telephone contact is established between the monitored person and the agency's host computer, the person will be given an 800 telephone number for making contact with the computer, so that the person incurs no telephone charges for making the call. Some agencies may use a 900 telephone number, imposing a modest charge for the call.

When contact is made, the host computer will screen the person making contact to make sure of the person's identify, and in some instances (e.g., where the person is supposed to remain in a certain geographic area) that the person is within an assigned area when the contact is made. Such determination is made using conventional telephone monitoring apparatus coupled to the host CPU that determines a particular area code and/or region from which a received telephone call originates.

The administrative case load management submodule provides three possible levels of screening when contact is made with the host computer. In a first level of screening, the computer will through voice synthesis, or equivalent, ask the person to identify himself or herself. Such identification will normally be accomplished by the person keying into the telephone a personal identification number (PIN). The computer is programmed to recognize such PIN regardless of whether it is keyed into a touch-tone telephone or a rotary dial telephone. Once the computer has received a valid PIN, it asks whether there have been any changes to the status of the individual since last making contact. The person may respond by keying in (or rotating in) a "1" for YES, or a "2" for NO. To help the person remember what information the computer has on file, the computer may, prior to asking this question, repeat what information it has. That is, as soon as a valid PIN is received, the computer responds with the person's name, address, and employer as stored in the computer memory files. If the person responds with a YES, indicating that there has been a change in his or her status since the last contact, then the person is requested to speak into the telephone what the changes are, e.g., a new address or a new employer. This new information is recorded for later review by agency personnel, who key it into the host CPU memory files. Some embodiments, adapted for use with touch-tone phone service, allow the person to key in the updated status information directly to the computer using the touch-tone key pad of the telephone.

In a second level of screening, which may be an option for use with the first level of screening, the person is further identified through his or her voice. In such screening, the computer has on file a previously entered sample of the individual's voice. The computer thus compares the voice spoken when the telecommunicative contact is established with the voice stored for the person having the PIN entered by the person. If there is a match, the person is allowed to continue with the updating of the status information. If there is not a match, that fact is noted, and a report is generated for the agency officer alerting him or her to the fact that someone other than the proper individual having a prescribed PIN attempted to contact the CPU for purposes of their regular check-in.

Figure 8A:
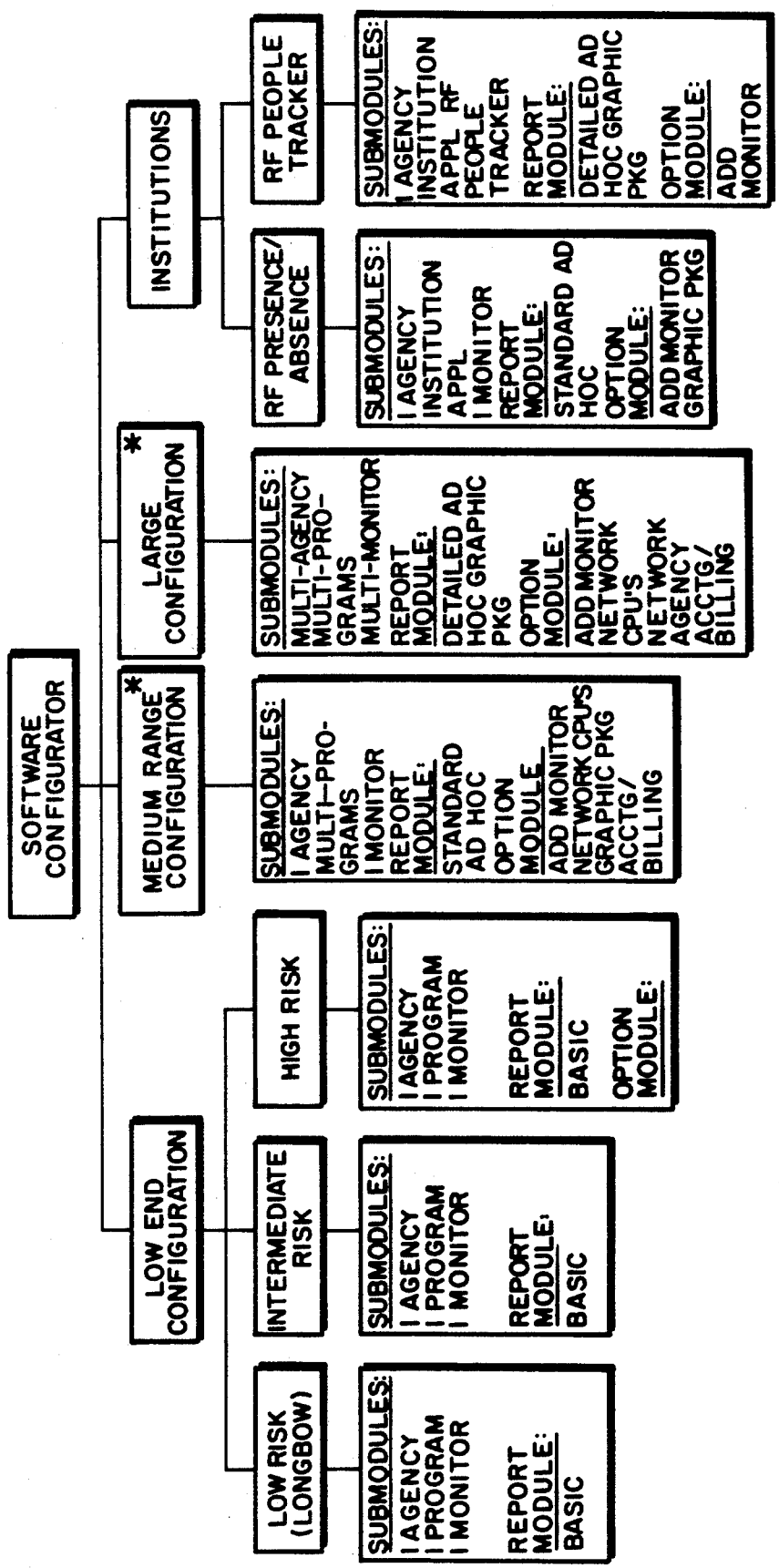
FIG. 8A depicts how the software modules of FIG. 7 may be combined to produce varying configurations of the monitoring system.
Figure 8B:
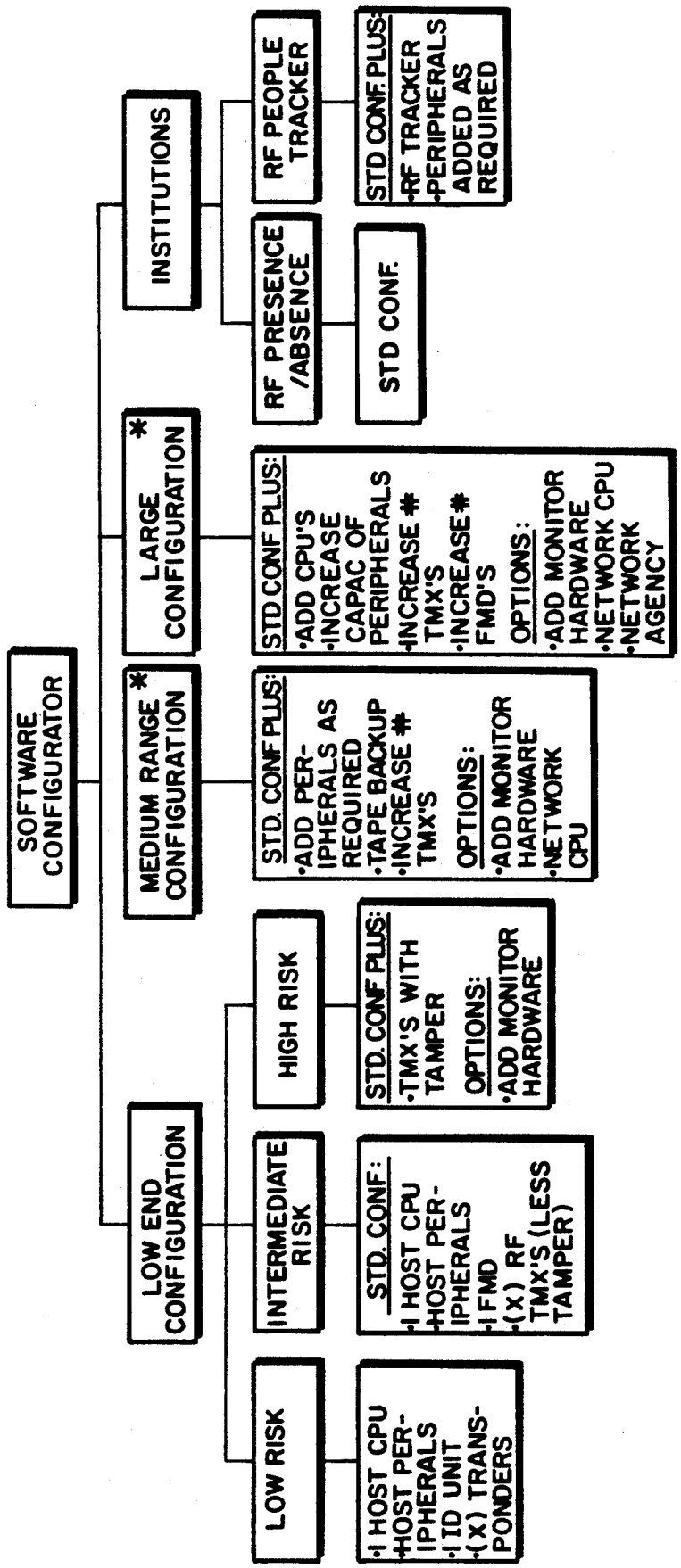
FIG. 8B depicts how various hardware modules may be configured in order to further add flexibility to the system.

FIGS. 8A and 8B illustrate representative software and hardware configurations for the monitoring and identification system of the present invention. These are divided into four classifications: Low End; Medium Range; Large; and Institutions. However, it is to be emphasized that even these classifications are merely exemplary. One of the significant advantages of the present invention is its flexibility, allowing it to be configured into a very large number of configurations, one of which will best fit a particular application. For example, for a low risk offender, it is probably sufficient to employ a transponder tag (i.e., one that transmits a signal only upon request), a single FMD at each offender's home, and a single CPU with standard peripherals (monitor and printer) at a desired remote monitoring site. The software needed by such a system would be an agency software submodule that utilizes a simple transponder program (e.g., verifying that the individual is at a specified location at a prescribed time, such as at home in bed after a specified curfew hour), and a basic report generating program.

For a more serious offender, the needed hardware might include an RF transmitting tag for each offender (one that periodically transmits an identifying signal) having tamper detect functions; one or more FMD's at critical locations so that the presence or absence of the individual at the specified locations could be monitored, and so that the whereabouts of the individual could be tracked relative to these locations; and at least one host CPU at a central location. In such a case, the software submodules loaded into the host CPU might include a software submodule that allows tracking from any of a plurality of monitors networked with the host CPU by the supervisory agency; a more sophisticated report generator, including graphics capabilities (so that charts and graphs can be included in any reports that are generated), as well as an alarm function that signals any detected tamper conditions.

As has been indicated previously, the present invention may optionally include the ability to sense various physiological or physical parameters of the monitored individual in order to detect if any alcohol or drugs or other proscribed activities have occurred. FIG. 9 is a table that depicts how certain types of activities affect body parameters that may be monitored. In FIG. 9, a "+" means that a small increase will likely occur in the measured parameter, while "++" or "+++" indicates a relatively larger increase will be seen. Similarly, a "−" indicates a small decrease of the measured parameter will likely occur in response to the indicated activity. A "+" and a "−" together indicate that the measured parameter could go either way. A "0" means there is no change in the measure parameter. The posture line shows whether the user is horizontal, vertical or either.

Thus, referring to FIG. 9 it is seen that body temperature, for example, will typically decrease slightly in response to sleeping, eating, taking cocaine and participating in violent activities. Body temperature will increase, however, most significantly in response to work, and somewhat in response to alcohol consumption. Similarly, the heart rate will increase somewhat in response to eating, consuming alcohol, taking cocaine, or engaging in violence; while it will increase significantly in response to working. The heart rate will decrease while sleeping. The other parameters shown in FIG.

8—leg size, activity, verbal, posture, and blood pressure—also vary roughly in the manner indicated as a function of the listed activities.

The monitoring system of the present invention selectively and optionally utilizes the information of FIG. 9, and similar known physiological-response information (now known or subsequently discovered) to detect the likelihood of occurrence of the listed events. Using known techniques in the medical and activity sensing art, heart rate, activity and posture are the easiest activities to sense reliably. For example, the activity and posture activities could be sensed using a simple mercury switch that is placed in the tag unit. Heart rate can be detected in any number of ways, from using a simple pressure detector or strain gauge in the strap or bands of the leg or wrist unit, to measuring variations in body impedance as explained below in connection with FIG. 12.

The leg size (or, in more general terms, the limb size) is known to swell whenever a Vasodilator such as alcohol is added to the blood stream. Hence, with reference to FIGS. 10A and 10B, the present invention detects variations in the size of a limb 75, such as the leg, by inserting a small balloon 77 on the inside of the strap 76 used to secure the tag unit 78 to the ankle. In operation, the balloon is occasionally blown up with a very light pressure so as not to disturb the wearer of the tag but with sufficient pressure to be able to make an accurate measurement of the diameter of the limb 75, the amount of volume added to the balloon providing a relative measure of the increase or decrease in size of the limb diameter. Such measurement techniques are known in the medical art.

Activity can also be sensed using a piezoelectric element, or a type of PVC (plastic) element that has piezo characteristics. Such a material emits an electrical signal whenever a mechanical stress is applied thereto. Further, the material is sensitive to heat and generates a voltage if a temperature change is sensed. (Actually, the temperature change causes the element to physically expand or contract, and this physical action is a mechanical stress that causes the electrical signal to be generated.) Hence, by placing a piezo-like material into the back of the case of the wrist or ankle unit, or in the strap, small changes in skin temperature can be sensed.

Two possible ways of accomplishing this temperature sensing are illustrated in FIGS. 11A and 11B. In FIG. 11B, the simplest sensing circuit is shown wherein the piezo element 130 is connected to a series of low noise, high impedance amplifiers 132 and 134. The output signal appearing on signal line 136 thus varies as a function of changes in skin temperature. If more sensitivity is required, the circuit of FIG. 11A is used. The circuit of FIG. 11A is the same as that of FIG. 11B except that a signal generator 138 is used to bias the piezo element 130 with an oscillation carrier signal. Changes in the skin temperature are thus sensed as a modulation of this signal carrier.

Referring next to FIG. 12, a technique for measuring or monitoring the pulse rate of an individual 140 is illustrated. This technique usually measures small resistance or impedance changes of the skin by placing sensors directly on the chest across the heart. Alternatively, a sensor can be placed on each arm. This stretches out the placement of the sensors, but accomplished the same goal. In accordance with the present invention, this same goal is achieved by placing a signal source on the wrist and placing a sensor on the ankle (or vice versa), as shown in FIG. 12. This allows the heart action to modulate the signal generated by one unit, which modulated signal is received by the other unit. Thus, the receiving unit, such as the ankle unit 44, acts like an RF receiver tuned to the frequency of the generating unit, such as the wrist unit 33. When the ankle unit 44 is properly configured, it is able to detect small changes in the received signal that are representative of the heart rate, or pulse rate, which rates are in turn indicative of activity of the individual 140.

An alternative technique for measuring the pulse rate (and possibly the temperature) is to detect the pulse rate directly at the wrist unit 33 using techniques known in the pulse monitoring art. This data is then transmitted either directly to the FMD 40 or down to the leg unit through the body, where the data is included in the identification information and sent back to the FMD 40.

Other types of sensors can be advantageously included within either the wrist unit 33 and/or the ankle unit 44 depending upon the particular needs of the application involved. If a sophisticated tamper circuit is needed, for example, a bone detector circuit could be included in the tag unit. A conventional transducer sends an ultrasonic signal into the leg or arm and expects to receive an echo signal back that represents a bone. If the echo signal is not present, or is not present with the right timing, the tag unit assumes that a tamper has occurred, and notifies the CPU (through the FMD) accordingly.

From the above description, it is evident that the present invention provides an adaptive monitoring and identification system that can be configured to suit most any application. Significantly, the invention need not be limited to applications of the corrections market. The invention also has application in the medical, security, home health care, and other markets where monitoring of individuals or objects must be performed.

As an example of the best mode of practicing the present invention, a description will now be given of a particular ADaptable Electronic Monitoring and Identification System, known as "ADEMIS", and referred to in the drawings by reference numeral 150. Such system will soon be manufactured and sold by B.I. Incorporated, assignee of this application, of Boulder, Colo., or a related entity. The ADEMIS system is depicted, in organizational block diagram format, in FIG. 13A. This figure, and its accompanying subfigures, FIGS. 13B–13D, illustrate the flexibility of ADEMIS, and also serve to teach more detail about the various ways in which ADEMIS can be configured and supported.

FIG. 13A illustrates the various categories of subsystems or support areas that are included within ADEMIS. As shown in FIG. 13A, ADEMIS 150 includes seven main components: (1) host operating software 160; (2) software application programs/modules 200; (3) hardware 300; (4) user documentation 400; (5) maintenance and support kits 500; (6) installation and training 600; and (7) system test simulator 700. Some of these components, such as user documentation, maintenance and support, installation and training, and system test simulator are not viewed, from an inventive point-of-view, as essential to operate the invention. The functional elements of the invention comprise simply the hardware 300 and the software 160 and 200. However, these other non-essential elements are still viewed as important to the long-term success of ADEMIS, for without them the system 150 would be short lived from a marketing point-of-view.

Figure 13B:
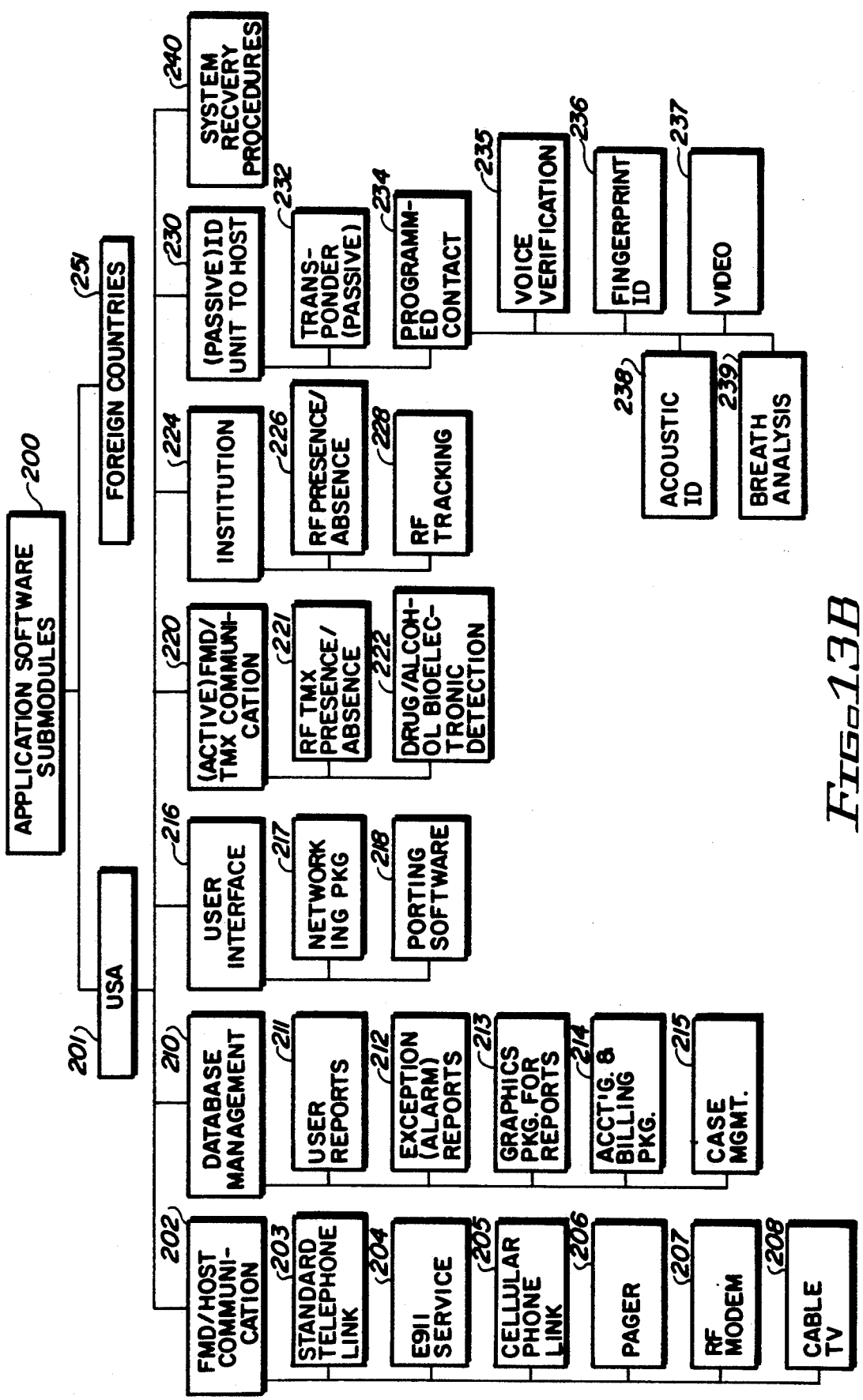
FIG. 13B is a chart of the system of FIG. 13A detailing the software processing requirements thereof.
Figure 13C:
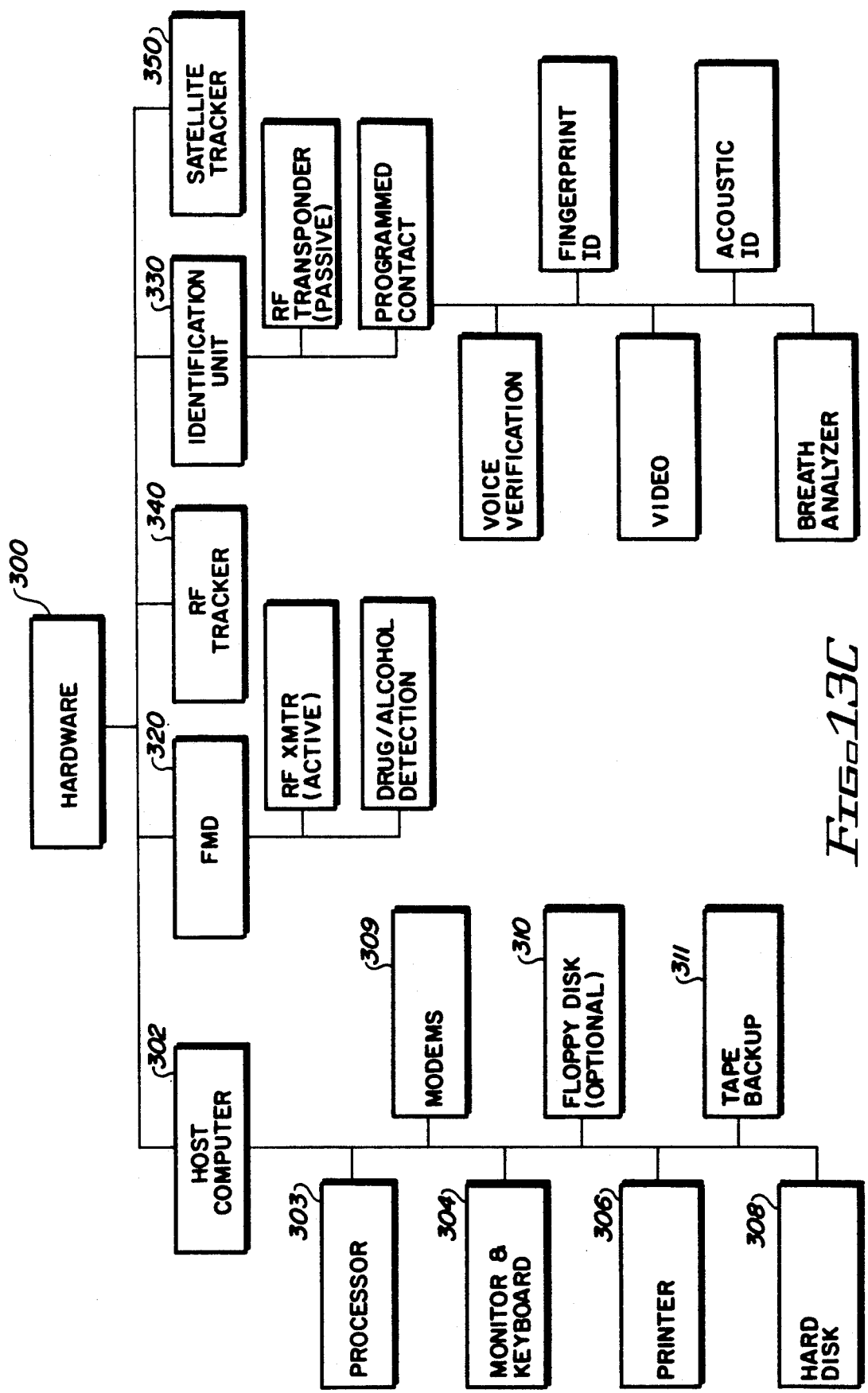
FIG. 13C is a chart of the system of FIG. 13A detailing the hardware requirements thereof.

In the category of application program software/modules 200, FIG. 13B details these requirements for the United States, referred to in FIG. 13B by reference numeral 201. (It is noted that similar, but different, requirements exist for other countries, referred to in FIG. 13B by reference numeral 251.) These U.S. software processing requirements 201 include a consideration of the following items: (1) FMD/Host Communications 202; (2) Database Management 210; (3) User Interface 216; (4) FMD/TMX Communications 220 (where "TMX" refers to an "active" tag unit, e.g., one that periodically transmits an identification signal that may or may not contain other information about the tag and the wearer of the tag as sensed by appropriate sensors); (5) Institution 224; (6) ID Unit/Host Communications 230 (where the "ID unit" refers to a "passive" identification unit that transmits an identification signal, and/or other identification information, only in response to an interrogation signal generated by a host device; and (7) System Recovery Procedures 240. Some of these items are self-explanatory. Others are described in more detail below.

FIG. 13B illustrates, for example, that the FMD/Host Communications 202 can be achieved in several ways. At the top of the list is a standard telephone link 203, as has been used in the prior art. Further, in some instances, it would be appropriate to establish an Emergency "911" telephone link 204. Such links are available in most parts of the United States to connect a telephone directly to an agency that provides emergency services, such as police, fire, hospital or ambulance. Moreover, and an especially important type of communication link in areas where regular telephone service is not fully established, a cellular telephone link 205 can be established. Further possible links between the FMD and the host CPU can be established using, for example, a pager 206, an RF modem 207, or a cable television (TV) communication link 208. The manner and technique for establishing any of these types of communication links is known to those skilled in the communication art.

FIG. 13B further identifies, under the category of FMD/TMX Communications 220, the types of software processing requirements that exist in view of the different kinds of information that are sent from the tag, or TMX, and the FMD. A typical signal from the tag unit simply identifies whether the tag is present or absent (221). However, as has been discussed, other information can optionally be made available, including the bioelectronic or biometric detection of drugs or alcohol (222).

FIG. 13B also illustrates a feature, not previously discussed in detail, of the ADEMIS 150. That is, it is contemplated that for some applications (230) the tag unit may communicate directly with the host CPU, thereby by-passing the FMD. For example, the tag may be configured to function primarily as a passive transponder device (232), including the capability of transmitting an identification signal of sufficient strength to be picked up by a receiver circuit coupled to the CPU, either directly or indirectly, in response to a trigger signal received from a transmitting circuit coupled to the CPU. Such a feature is most useful in a "tracking" application, in which case the receiving and transmitting circuits used by the CPU, some of which may be portable, comprise an RF Tracker unit of a type known in the art. Further, programmed contact (234) with the wearer of the tag may provide useful biometric or other information that further serves to identify the wearer of the tag. For example, phone voice verification (235), electronic identification of fingerprints (236), video signals (237), acoustic identification (238), home voice verification (233), and breath analyzer signals (239) could all be used to provide a more positive identification of the wearer of the tag and his or her condition. The techniques for generating such biometric signals, e.g., electronic voice, acoustic, video and fingerprint identification signals, as well as electronic breath analysis signals, are known in the art.

It is noted that phone voice verification (235) contemplates the use of only a telephone at the remote location, with the electronic circuitry that analyzes the voice response being located at the central location, typically within the host CPU. In contrast, home voice verification (233) contemplates the electronic voice verification circuitry being located at the remote site. In such instance, such remote circuitry generates a verification signal indicating whether the correct voice has been identified, which verification signal is communicated to the central location over the established telecommunicative link.

FIG. 13B also illustrates the flexibility of the system 150 relative to the various user interface(s) (216) that could be employed. For example, while it is contemplated that different CPU's could be networked together (217), thereby allowing the operating software (160) and the application software (200) to be easily shared between such units; this software is written in such a way that it can be easily ported (218) from one device to another through the use of removable magnetic storage media, such as floppy disks or cassette tapes, optical disks, or other equivalent data transfer media. Such transfer of the software can advantageously occur, with minimum interface difficulties, even though the CPU hardware at the receiving location may present an entirely different hardware configuration than the hardware configuration present at the source location, i.e., even though the hardware systems may be generally thought of as "incompatible" systems.

FIG. 13C details the various hardware components or subsystems (300) that may be optionally included as part of the ADEMIS system 150. These components include a host CPU 302, an FMD 320, an identification unit or tag 330, an RF tracking system 340, and/or a satellite tracking system 350.

The CPU 302 may be of conventional design, and typically includes a processing unit (303), monitor and keyboard (304), a printer (306), a hard disk (308), one or mode floppy disk drives (310), a modem (309), and a tape backup system (311). A fax unit (312) may also be coupled to the host computer and/or established telecommunicative link for sending or receiving facsimile transmissions to the remote site. By way of illustration, the basic processing unit (303) may be an 80386 based system, such as the IBM II, or Compaq, or numerous other equivalent processors. The hard disk storage unit (308) may include 20–40 Mbytes of hard disk storage, which units are available from numerous manufacturers.. The floppy drive (310) can be selected to have a desired storage capacity, ranging from 360 Kbytes to 2.4 Mbytes, in a suitable size (such as 3.5 or 5 and ¼ inch diskettes). The other peripheral equipment (306, 309, 311, 312) can be any commercially available equipment—printers, modems, monitors, data backup systems, fax boards, fax units, etc.—that is readily available in the computer market.

The host operating system (160, FIG. 13A) used with the host CPU (302, FIG. 13C) is preferably OS/2; but an MS-DOS operating system could also be used. The use of either operating system is well known and documented in the art. Moreover, both operating systems are more-or-less compatible with each other, thereby allowing the bulk of the application programs (which programs form the basis of most the software modules used with the system) to be used without modification regardless of which operating system is used. Alternatively, if a Macintosh II hardware configuration is used, a UNIX operating system can be utilized for the ADEMIS system.

Finally, FIG. 13D illustrates additional detail associated with the user documentation (400), maintenance and support kits (500), installation and training (600), and system test simulator (700) of the ADEMIS system 150. As has been explained, these areas are considered as additional enhancements to the main components of the invention (hardware and software) to help ensure that the ADEMIS system is used and maintained properly and successfully. A detailed understanding of these areas is not necessary in order to understand and practice the present invention. Accordingly, no further detail concerning these areas will be provided herein. That which is presented in FIG. 13D is believed to be self-explanatory.

As is evident from the above descriptions, the ADEMIS system provides a great deal of flexibility in how it is configured and operated. Key to this flexibility are the application programs, or software modules, that control the operation of the system. The requirements for such programs or modules were discussed previously in connection with FIG. 13B. Much of the detail of such programs depends upon the particular configuration that is selected. However, in general, such programs or software modules define the basic operation for a given application, call common subroutines as required, initiate contact with and/or respond to interrogation signals from the FMD, perform basic processing steps with data obtained from the tag units through the FMD, and perform other functions that are more-or-less common to most of the configurations contemplated by the ADEMIS system. It is submitted that those skilled in the art, given the description of the ADEMIS system presented herein, could write such application software programs for a particular application as the need arises.

While the invention described herein has been described with reference to specific embodiments and applications thereof, numerous variations and modifications could be made thereto by those skilled in the art without departing from the spirit and scope of the invention as claimed. Accordingly, the true scope of the invention should be determined with reference to the claims set forth below.

What is claimed is:

1. An adaptable personnel monitoring and identification system comprising:
    a tag carried by a first individual of a population of individuals being monitored, said tag including means for transmitting a unique identification signal;
    a central processing unit (CPU) in telecommunicative contact with said tag; and
    means for establishing telecommunicative contact between a second individual of said population of individuals and said CPU;
    said CPU having a plurality of software program submodules adapted to be transferred thereto and selectively stored therein, each one of said software program submodules comprising a control program that can be used to help control said personnel monitoring and identification system for a particular application;
    a first one of said software control programs comprising a monitoring submodule that receives said unique identification signal from said tag, and processes said unique identification signal in order to confirm that the tag, and hence the first individual carrying said tag, is at a prescribed remote location at a specified time;
    a second one of said software control programs comprising an administrative case load management submodule that: (1) verifies the identity of said second individual once said telecommunicative contact is established with said CPU, (2) verifies that the second individual has contacted the CPU within an obligated contact time period, and (3) verifies the status of the second individual;
    whereby said population of individuals being monitored by said system may include both individuals like the first individual carrying a tag, and individuals like the second individual who do not carry a tag but who are obligated to regularly contact the CPU to report their status.

2. The adaptable personnel monitoring and identification system as set forth in claim 1 wherein said case load management submodule automatically tracks a plurality of individuals who are required to regularly provide notice of their current status.

3. The adaptable personnel monitoring and identification system as set forth in claim 2 wherein said administrative case load management submodule instructs individuals in telecommunicative contact with said system to uniquely identify themselves and allows such individuals to update their status if there has been a change in their status since last contacting said system.

4. The adaptable personnel monitoring and identification system as set forth in claim 3 wherein said administrative case load management submodule includes means for uniquely identifying said persons based on assigned personnel identification numbers.

5. The adaptable personnel monitoring and identification system as set forth in claim 3 wherein said administrative case load management submodule includes means for uniquely identifying said persons based on their voice.

6. The adaptable personnel monitoring and identification system as set forth in claim 3 wherein said administrative case load management submodule includes means for identifying a location at which an individual in telecommunicative contact with said system is located at the time said telecommunicative contact is established.

7. The adaptable personnel monitoring and identification system as set forth in claim 6 wherein said administrative case load management submodule further includes means for verifying whether said location at which said person is at when in telecommunicative contact with said system is an assigned location.

8. An adaptable personnel monitoring and identification system for monitoring a population of individuals being monitored comprising:
    means for establishing telecommunicative contact between a given individual of said population of individuals, under obligation to make regular status reports, and a central processing unit (CPU) in a central location remote from said given individual, said CPU having status information stored therein for each individual of said population of individuals being monitored; and an administrative case load management software program submodule adapted to be transferred to and selectively stored in said CPU, said administrative case load management submodule including means for verifying the identity of said given individual once telecommunicative contact is established with said CPU, and means for automatically requesting whether the status information stored in said CPU for said given individual has changed since said given individual last contacted said CPU.

9. The personnel monitoring and identification system as set forth in claim 8 wherein said administrative case load management submodule includes means for allowing said given individual to change the status information stored in said CPU in the event such status information has changed.

10. The personnel monitoring and identification system as set forth in claim 9 wherein said verifying means of said administrative case load management submodule includes means for verifying that a personal identification number (PIN) provided by said given individual, once telecommunicative contact has been established, is a valid PIN.

11. The personnel monitoring and identification system as set forth in claim 9 wherein said verifying means of said administrative case load management submodule includes means for verifying that a voice response provided by said given individual once telecommunicative contact has been established is a voice response unique to said given individual.

12. The personnel monitoring and identification system as set forth in claim 9 wherein said verifying means of said administrative case load management submodule includes means for verifying that said given individual is within a prescribed geographic area when said telecommunicative contact is established.

* * * * *